(12) United States Patent
Vince et al.

(10) Patent No.: US 10,925,851 B2
(45) Date of Patent: Feb. 23, 2021

(54) USE OF TOSEDOSTAT AND RELATED COMPOUNDS AS ANALGESICS

(71) Applicant: Regents of the University of Minnesota, Minneapolis, MN (US)

(72) Inventors: Robert Vince, Minneapolis, MN (US); Rohit Singh, Minneapolis, MN (US); Swati Sudhakar More, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 16/353,974

(22) Filed: Mar. 14, 2019

(65) Prior Publication Data

US 2019/0282531 A1    Sep. 19, 2019

Related U.S. Application Data

(60) Provisional application No. 62/643,596, filed on Mar. 15, 2018.

(51) Int. Cl.
   *A61K 31/216*  (2006.01)
   *A61P 29/00*   (2006.01)
   *A61K 45/06*   (2006.01)

(52) U.S. Cl.
   CPC ............ *A61K 31/216* (2013.01); *A61K 45/06* (2013.01); *A61P 29/00* (2018.01)

(58) Field of Classification Search
   None
   See application file for complete search history.

(56) References Cited

U.S. PATENT DOCUMENTS

| | | | |
|---|---|---|---|
| 4,380,535 A | 4/1983 | Sarantakis et al. | |
| 6,169,075 B1 | 1/2001 | Pearson et al. | |
| 6,306,881 B1 * | 10/2001 | Ayscough | A61K 31/381 514/327 |
| 6,462,023 B1 | 10/2002 | Pearson et al. | |
| 6,790,834 B1 * | 9/2004 | Pearson | A61K 31/4406 514/506 |
| 9,549,969 B2 | 1/2017 | Hoffman | |
| 2016/0068522 A1 | 3/2016 | Guilford et al. | |

FOREIGN PATENT DOCUMENTS

WO    1999046241    9/1999

OTHER PUBLICATIONS

Lowenberg et al., J. Clin. Oncol., 2010, vol. 28, No. 28, pp. 4333-4338 (Year: 2010).*
Fryer et al., PLoS ONE, 2013, vol. 8, No. 2, e57641 (Year: 2013).*
Jia, M , et al., "The analgesic activity of Bestatin as a potent APN inhibitor", Frontiersin.org 4(50), 10 pages (2010).
Le Guen, S , et al., "Pain management by a new series of dual inhibitors of enkephalin degrading enzymes: long lasting antinociceptive properties and potentiation by CCK2antagonist or methadone", Pain 104 (1-2), 139-148 (2003).
Rougeot, C , et al., "Sialorphin, a natural inhibitor of rat membrane-bound neutral endopeptidase that displays analgesic activity", PNAS 100(14), 8549-8554 (2003).
Singh, R , et al., "Discovery of Anticancer Clinical Candidate, Tosedostat, As an Analgesic Agent", ACS Chem Neurosci doi: 10.1021/acschemneuro.9b00230. [Epub ahead of print], 11 pages (2019).

* cited by examiner

*Primary Examiner* — My-Chau T. Tran
(74) *Attorney, Agent, or Firm* — Viksnins Harris Padys Malen LLP

(57) ABSTRACT

The invention provides methods and compositions for producing analgesia in an animal.

23 Claims, 15 Drawing Sheets

Batimastat (2)

| | |
|---|---|
| Met-Enk (3): | Tyr-Gly-Gly-Phe-Met |
| Leu-Enk (4): | Tyr-Gly-Gly-Phe-Leu |
| β-Endorphin: | Tyr-Gly-Gly-Phe-Leu-Thr-Ser-Glu-... |
| Dynorphin A: | Tyr-Gly-Gly-Phe-Leu-Arg-Arg-Ile-... |
| Dynorphin B: | Tyr-Gly-Gly-Phe-Leu-Arg-Arg-Gln-... |

|  | AUC (h*nmol/L) | Brain/Plasma Ratio |
|---|---|---|
| Brain | 26.27375 | 0.034 |
| Plasma | 762.2025 | |

USE OF TOSEDOSTAT AND RELATED COMPOUNDS AS ANALGESICS

CROSS-REFERENCE TO RELATED APPLICATIONS

This application claims priority to U.S. Provisional Application No. 62/643,596, filed Mar. 15, 2018. The entire content of the application referenced above is hereby incorporated by reference herein.

BACKGROUND

International Patent Application Publication Number WO1999/046241 and U.S. Pat. Nos. 6,169,075 and 6,462,023 describe compounds of Formula (I):

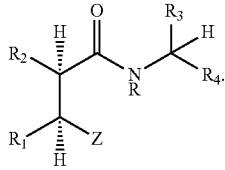

The compounds of Formula (I) are reported to have activity as inhibitors of the proliferation of a range of rapidly dividing tumor cells, for example melanoma and/or lymphoma cells. One of these compounds Tosedostat (also known as CHR-2797; CA REG NO 238750-77-1),

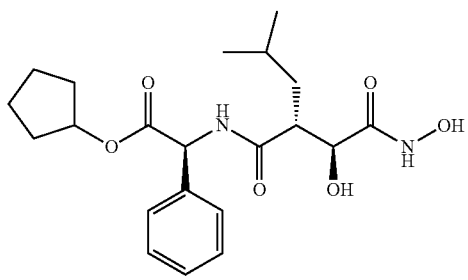 [SMILES: CC(C)C[C@@H](C(=O)N[C@H](C(=O)OC1CCCC1)c1ccccc1)[C@H](O)C(=O)NO]

is an aminopeptidase inhibitor that is currently in phase II clinical trial for treatment of certain blood related cancers.

Pain represents a major health and economic problem throughout the world. Among current analgesic drugs, the opioid class of compounds is widely used for pain treatment. Morphine and related opioids produce their analgesia primarily through their agonist action at mu opioid receptors. Unfortunately, opioids have high abuse potential and often produce various undesirable conditions such as dependency, addiction, and increased tolerance. Moreover, opioids can induce severe adverse effects such as respiratory depression, and sedation, etc.

Currently, there is a need for additional agents and methods that can be used to treat pain. Ideally, such agents and methods will produce fewer unwanted side effects compared to currently available therapies.

SUMMARY

Applicant has discovered that tosedostat possesses analgesic properties. The analgesic properties of tosedostat are believed to occur outside the brain as a result of the compounds blocking the inactivation of endogenous opioid peptides, called enkephalins, by peptidases (Enkephalinases), allowing these peptides to exist in the body for a longer period of time to produce a natural analgesic effect. Accordingly, tosedostat and similar compounds may have the potential to replace current analgesic compounds by providing pain-relieving effects with reduced adverse effects. Additionally, these compounds may be able to work in combination with current analgesics, thus providing more options for pain relief.

Accordingly, in one embodiment, the invention provides a method for producing analgesia in an animal comprising administering to the animal a compound of formula (I):

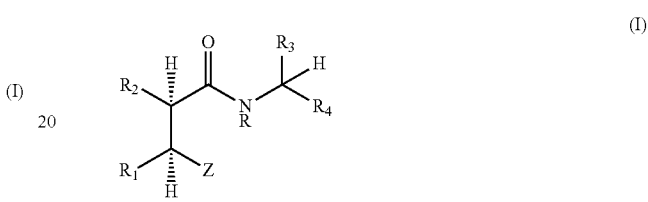

wherein:

R is hydrogen or $(C_1-C_6)$alkyl;

$R_1$ is hydrogen, $(C_1-C_6)$alkyl, $(C_2-C_6)$alkenyl, phenyl, phenyl$(C_1-C_6)$alkyl, phenyl$(C_2-C_6)$alkenyl, heterocyclyl, heterocyclyl$(C_1-C_6)$alkyl, hydroxyl, $(C_1-C_6)$alkoxy, $-NH_2$, $-C(=O)NH_2$, $(C_1-C_6)$alkylamino, di$(C_1-C_6)$alkylamino, mercapto, $(C_1-C_6)$alkylthio, (heteroaryl)thio$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl, mercapto$(C_1-C_6)$alkyl, carboxy$(C_1-C_6)$alkyl, lower alkyl substituted by carbamoyl, mono$((C_1-C_6)$alkyl)carbamoyl, di$((C_1-C_6)$alkyl)carbamoyl, di$((C_1-C_6)$alkyl)amino, or carboxy-lower alkanoylamino, $R^a$, or a group $BSO_nA$-; or $R^1$ and $R^2$ taken together with the atoms to which they are attached form a 4-, 5-, 6-, or 7-membered saturated or partially unsaturated carbocycle or a 4-, 5-, 6-, or 7-membered saturated or partially unsaturated heterocycle that comprises carbon and one or two heteroatoms selected from O, S, and $NR^d$, wherein $R^d$ is H or $(C_1-C_4)$alkyl;

n is 0, 1 or 2;

B is hydrogen, $(C_1-C_6)$alkyl, phenyl, heterocyclyl, $(C_1-C_6)$alkanoyl, or phenyl-C(=O)—;

A is $(C_1-C_6)$alkylene, $R^a$ is a cycloalkyl, a cycloalkenyl, or a non-aromatic heterocyclic ring containing up to 3 heteroatoms, any of which may be (i) substituted by one or more substituents selected from $(C_1-C_6)$alkyl, $(C_2-C_6)$alkenyl, halo, cyano, carboxy, $-CO_2R^b$, $-CONH_2$, $-CONHR^b$, $-CON(R^b)_2$, $-OH$, $-OR^b$, oxo, $-SH$, $-SR^b$, $-NHCOR^b$, and $NHCO_2R^b$; or (ii) fused to a cycloalkyl or heterocyclic ring;

$R^b$ is $(C_1-C_6)$alkyl or benzyl;

$R_2$ is $(C_1-C_{12})$alkyl, $(C_2-C_{12})$alkenyl, $(C_2-C_{12})$alkynyl, phenyl$(C_1-C_6)$alkyl-, heteroaryl$(C_1-C_6)$alkyl-, phenyl$(C_2-C_6)$alkenyl-, heteroaryl$(C_2-C_6)$alkenyl-, phenyl$(C_2-C_6)$alkynyl-, heteroaryl$(C_2-C_6)$alkynyl-, cycloalkyl$(C_1-C_6)$alkyl-, cycloalkyl$(C_2-C_6)$alkenyl-, cycloalkyl$(C_2-C_6)$alkynyl-, cycloalkenyl$(C_1-C_6)$alkyl-, cycloalkenyl$(C_2-C_6)$alkenyl-, cycloalkenyl$(C_2-C_6)$alkynyl-, phenyl$(C_1-C_6)$alkyl-O$(C_1-C_6)$alkyl-, or heteroaryl$(C_1-C_6)$alkyl-O—$(C_1-C_6)$alkyl- any one of which may be optionally substituted by $(C_1-C_6)$alkyl, $(C_1-C_6)$alkoxy, halo, cyano, phenyl, or phenyl that is optionally substituted by $(C_1-C_6)$alkyl, $(C_1-C_6)$alkoxy, halo, or cyano;

$R_3$ is the side chain of a natural or a non-natural α-amino acid in which any functional groups may be protected;

$R_4$ is an ester group, a thioester group, aminocarbonyl, $(C_1-C_6)$alkylaminocarbonyl, or di$(C_1-C_6)$alkylaminocarbonyl; and Z is selected from —CONHOH, —COOR$^c$, —CONHOR$^c$, —CONR$^c$OH, —CONHS(O)$_2$R$^c$, —CONH$_2$, —CONHR$^c$, and —P(O)(OH)$_2$, wherein R$^c$ is $(C_1-C_4)$alkyl, aryl$(C_1-C_4)$alkyl-, or heteroaryl$(C_1-C_4)$alkyl-;

or a pharmaceutically acceptable salt thereof;

wherein any phenyl or heterocyclyl of $R_1$ is optionally substituted with up to four substituents, each of which independently may be selected from $(C_1-C_6)$alkyl, $(C_1-C_6)$alkoxy, hydroxy, mercapto, $(C_1-C_6)$alkylthio, amino, halo, nitro, trifluoromethyl, —COOH, —CONH$_2$, cyano, —COOR$^A$, —COONHR$^A$ or —COONR$^A$R$^A$ wherein R$^A$ is a $(C_1-C_6)$alkyl group or the residue of a natural alpha-amino acid.

The invention also provides a pharmaceutical composition comprising 1) a compound of formula (I) or a pharmaceutically acceptable salt thereof, 2) an analgesic agent, and 3) an excipient.

Tosedostat possesses analgesic properties that are primarily restricted to periphery outside the brain. Compounds of formula (I) could provide analgesic effect by binding to peripheral receptors, allowing the natural analgesics (enkephalins) to exist for longer period of time than they would normally exist.

Steroidal and non-steroidal anti-inflammatory drugs have been described as analgesics, but they suffer from serious side-effects such as (i) ulcers (ii) hypersensitivity (iii) bleeding (iv) major organ toxicity (especially, kidney and liver). Combination therapies with other opiates or adrenergic agonists also produce respiratory depression and sedative side effects, and thus, result in low patient compliance. Stopping the breakdown of peptidases avoids overstimulation of pain related receptors. This results in no development of dependency, addiction, or increased tolerance to analgesic effects, since the compound is restricted to periphery.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION

Figure 1:
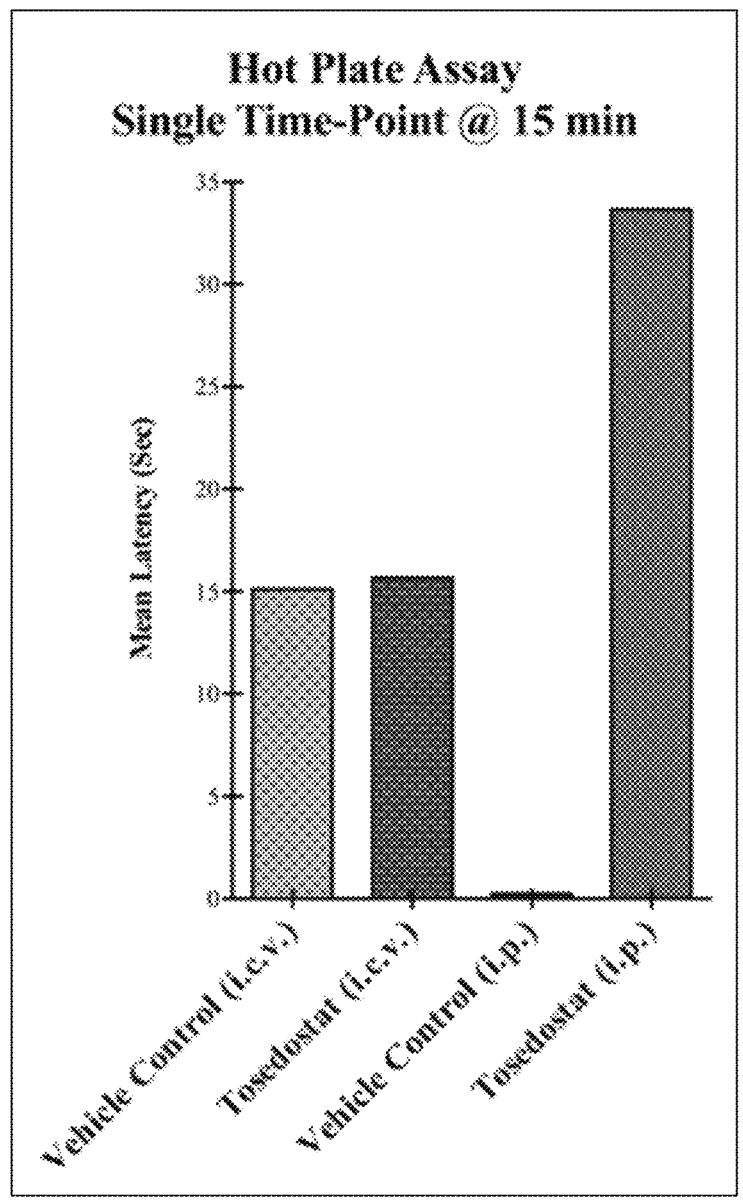
FIG. 1 shows preliminary evaluation of analgesic potency of tosedostat at 15-minute time-point after i.c.v. and i.p. administration of the test compound. See Example 1.

The terms "treat", "treatment", or "treating" to the extent it relates to a disease or condition includes inhibiting the disease or condition, eliminating the disease or condition, and/or relieving one or more symptoms of the disease or condition. The terms "treat", "treatment", or "treating" also refer to both therapeutic treatment and/or prophylactic treatment or preventative measures, wherein the object is to prevent or slow down (lessen) an undesired physiological change or disorder, such as, for example, the development or spread of cancer. For example, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. "Treat", "treatment", or "treating," can also mean prolonging survival as compared to expected survival if not receiving treatment. Those in need of treatment include those already with the disease or disorder as well as those prone to have the disease or disorder or those in which the disease or disorder is to be prevented. In one embodiment "treat", "treatment", or "treating" does not include preventing or prevention, The phrase "therapeutically effective amount" or "effective amount" includes but is not limited to an amount of a compound of the that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "mammal" as used herein refers to humans, higher non-human primates, rodents, domestic, cows, horses, pigs, sheep, dogs and cats. In one embodiment, the mammal is a human. The term "patient" as used herein refers to any animal including mammals. In one embodiment, the patient is a mammalian patient. In one embodiment, the patient is a human patient.

As used herein the term "$(C_1-C_6)$alkyl" or "lower alkyl" means a straight or branched chain alkyl moiety having from 1 to 6 carbon atoms, including for example, methyl, ethyl, n-propyl, isopropyl, n-butyl, isobutyl, sec-butyl, t-butyl, n-pentyl and n-hexyl.

The term "$(C_2-C_6)$alkenyl" means a straight or branched chain alkenyl moiety having from 2 to 6 carbon atoms having at least one double bond of either E or Z stereochemistry where applicable. This term would include, for example, vinyl, allyl, 1- and 2-butenyl and 2-methyl-2-propenyl.

The term "$(C_2-C_6)$alkynyl" refers to straight chain or branched chain hydrocarbon groups having from two to six carbon atoms and having in addition one triple bond. This term would include for example, ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl.

The term "cycloalkyl" means a saturated alicyclic moiety having from 3-8 carbon atoms and includes, for example, cyclohexyl, cyclooctyl, cycloheptyl, cyclopentyl, cyclobutyl, and cyclopropyl.

The term "cycloalkenyl" means an unsaturated alicyclic moiety having from 4-8 carbon atoms and includes, for example, cyclohexenyl, cyclooctenyl, cycloheptenyl, cyclopentenyl, and cyclobutenyl. In the case of cycloalkenyl rings of from 5-8 carbon atoms, the ring may contain more than one double bond.

The term "aryl" means an unsaturated aromatic carbocyclic group which is monocyclic (e.g. phenyl) or polycyclic (e.g. naphthyl).

The unqualified term "heterocyclyl" or "heterocyclic" means (i) a 5-7 membered heterocyclic ring containing one or more heteroatoms selected from S, N and 0, and optionally fused to a benzene ring, including for example, pyrrolyl, furyl, thienyl, piperidinyl, imidazolyl, oxazolyl, thiazolyl, thiadiazolyl, pyrazolyl, pyridinyl, pyrrolidinyl, pyrimidinyl, morpholinyl, piperazinyl, indolyl, benzimidazolyl, maleimido, succinimido, phthalimido, 1,2-dimethyl-3,5-dioxo-1,2,4-triazolidin-4-yl, 3,4,4-trimethyl-2,5-dioxo-1-imidazolidinyl, 2-methyl-3,5-dioxo-1,2,4-oxadiazol-4-yl, 3-methyl-2,4,5-trioxo-1-imidazolinyl, 2,5-dioxo-3-phenyl-1-imidazolidinyl, 2-oxo-1-pyrrolidinyl, 2,5-dioxo-1-pyrrolidinyl or 2,6-dioxopiperidinyl, or (ii) a naphthalimido (i.e. a 1,3-dihydro-1,3-dioxo-2H-benz[f]isoindol-2-yl), 1,3-dihydro-1-oxo-2H-benz[f]isoindol-2-yl, 1,3-dihydro-1,3-dioxo-2H-pyrrolo[3,4-b]quinolin-2-yl, or 2,3-dihydro-1,3-dioxo-1H-benz[d,e]isoquinolin-2-yl group).

The term "heteroaryl" means a 5-7 membered substituted or unsubstituted aromatic heterocycle containing one or more heteroatoms. Illustrative of such rings are thienyl, furyl, pyrrolyl, imidazolyl, thiazolyl, pyrazolyl, isoxazolyl, isothiazolyl, trizolyl, thiadiazolyl, oxadiazolyl, pyridinyl, pyridazinyl, pyrimidinyl, pyrazinyl, and triazinyl.

The term "ester" or "esterified carboxyl group" means a group $R_9O(C=O)$— in which $R_9$ is the group characterizing the ester, notionally derived from the alcohol $R_9OH$. For example, in one embodiment, $R_9$ can be $(C_1-C_6)$alkyl, $(C_3-C_6)$cycloalkyl, or $(C_5-C_6)$cycloalkenyl, which $(C_1-C_6)$alkyl, $(C_3-C_6)$cycloalkyl, and $(C_5-C_6)$cycloalkenyl is optionally substituted with one or more halo.

The term "thioester" means a group $R_9S(C=O)$— or $R_9S(C=S)$— or $R_9O(C=S)$— in which $R_9$ is the group characterizing the thioester, notionally derived from the alcohol $R_9OH$ or the thioalcohol $R_9SH$. For example, in one embodiment, $R_9$ can be $(C_1-C_6)$alkyl, $(C_3-C_6)$cycloalkyl, or $(C_5-C_6)$cycloalkenyl, which $(C_1-C_6)$alkyl, $(C_3-C_6)$cycloalkyl, and $(C_5-C_6)$cycloalkenyl is optionally substituted with one or more halo.

Unless otherwise specified in the context in which it occurs, the term "substituted" as applied to any moiety herein means substituted with up to four substituents, each of which independently may be $(C_1-C_6)$alkyl, $(C_1-C_6)$alkoxy, hydroxy, mercapto, $(C_1-C_6)$alkylthio, amino, halo, nitro, trifluoromethyl, —COOH, —CONH$_2$, cyano, —COOR$^A$, —COONHR$^A$ or —COONR$^A$R$^A$ wherein R$^A$ is a $(C_1-C_6)$alkyl group or the residue of a natural alpha-amino acid The term "side chain of a natural or non-natural alpha-amino acid" means the group $R^1$ in a natural or non-natural amino acid of formula $NH_2$—CH(R$^1$)—COOH. Examples of side chains include those of alanine, arginine, asparagine, aspartic acid, cysteine, cystine, glutamic acid, histidine, 5-hydroxylysine, 4-hydroxyproline, isoleucine, leucine, lysine, methionine, phenylalanine, proline, serine, threonine, tryptophan, tyrosine, valine, α-aminoadipic acid, α-amino-n-butyric acid, 3,4-dihydroxyphenylalanine, homoserine, α-methylserine, ornithine, pipecolic acid, and thyroxine. Natural alpha-amino acids which contain functional substituents, for example amino, carboxyl, hydroxy, mercapto, guanidyl, imidazolyl, or indolyl groups in their characteristic side chains include arginine, lysine, glutamic acid, aspartic acid, tryptophan, histidine, serine, threonine, tyrosine, and cysteine. When $R_3$ in the compounds of the invention is one of those side chains, the functional substituent may optionally be protected. An example of a side chain of a non-natural alpha-amino acid is phenyl.

The term "protected" when used in relation to a functional substituent in a side chain of a natural alpha-amino acid means a derivative of such a substituent which is substantially non-functional. For example, carboxyl groups may be esterified (for example as a $(C_1-C_6)$alkyl ester), amino groups may be converted to amides (for example as a NHCO$(C_1-C_6)$alkyl amide) or carbamates (for example as an NHC(=O)O$(C_1-C_6)$alkyl or NHC(=O)OCH$_2$Ph carbamate), hydroxyl groups may be converted to ethers (for example an O$(C_1-C_6)$alkyl or a O$(C_1-C_6)$alkylphenyl ether) or esters (for example a OC(=O)$(C_1-C_6)$alkyl ester) and thiol groups may be converted to thioethers (for example a tert-butyl or benzyl thioether) or thioesters (for example a SC(=O)$(C_1-C_6)$alkylthioester).

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Salts of the compounds of the invention include physiologically acceptable acid addition salts for example hydrochlorides, hydrobromides, sulphates, methane sulphonates, p-toluenesulphonates, phosphates, acetates, citrates, succinates, lactates, tartrates, fumarates and maleates. Salts may also be formed with bases, for example sodium, potassium, magnesium, and calcium salts. Salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The pharmaceutical compositions of the invention can comprise one or more excipients. When used in combination with the pharmaceutical compositions of the invention the term "excipients" refers generally to an additional ingredient that is combined with the compound of formula (I) or the pharmaceutically acceptable salt thereof to provide a corresponding composition. For example, when used in combination with the pharmaceutical compositions of the invention the term "excipients" includes, but is not limited to: carriers, binders, disintegrating agents, lubricants, sweetening agents, flavoring agents, coatings, preservatives, and dyes.

The compounds of formula I or salt thereof can be formulated as pharmaceutical compositions and administered to a mammalian host, such as a human patient in a variety of forms adapted to the chosen route of administration, i.e., orally or parenterally, by intravenous, intramuscular, intrathecal, topical or subcutaneous routes.

Thus, the formula I or salt thereof may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The compound of formula I or salts thereof may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the compound of formula I or salt thereof may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I or salts thereof can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Embodiments

The following non-limiting specific values are identified for the groups herein.

A specific value for R is hydrogen.

A specific value for $R_1$ is hydroxyl.

A specific value for $R_1$ is (heteroaryl)thio($C_1$-$C_6$)alkyl.

A specific value for $R_1$ is 2-thienylthiomethyl.

A specific value for $R_2$ is ($C_1$-$C_{12}$)alkyl.

A specific value for $R_3$ is phenyl.

A specific value for $R_3$ is benzyl.

A specific value for $R_3$ is 2-methylpropyl.

A specific value for $R_4$ is cycloalkyl-O—C(=O)—.

A specific value for $R_4$ is cyclopentoxycarbonyl.

A specific value for $R_4$ is methylaminocarbonyl.

A specific compound or salt is tosedostat:

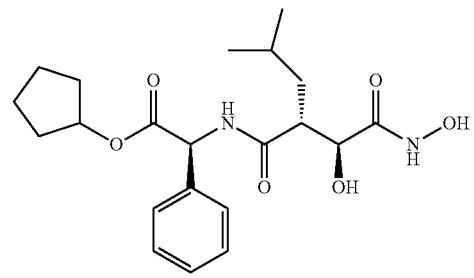

or a pharmaceutically acceptable salt thereof.

A specific compound or salt is batimastat:

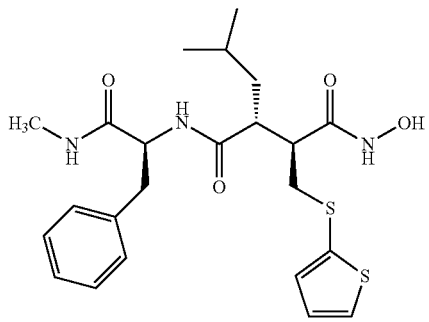 [SMILES: CNC(=O)[C@H](Cc1ccccc1)NC(=O)[C@H](CC(C)C)[C@H](CSc1cccs1)C(=O)NO]

or a pharmaceutically acceptable salt thereof.

For a specific compound of formula (I) or pharmaceutically acceptable salt thereof:

R is hydrogen or $(C_1-C_6)$alkyl;

$R_1$ is hydrogen, $(C_1-C_6)$alkyl, $(C_2-C_6)$alkenyl, phenyl, phenyl$(C_1-C_6)$alkyl, phenyl$(C_2-C_6)$alkenyl, heterocyclyl, heterocyclyl$(C_1-C_6)$alkyl, hydroxyl, $(C_1-C_6)$alkoxy, —$NH_2$, —C(=O)$NH_2$, $(C_1-C_6)$alkylamino, di$(C_1-C_6)$alkylamino, mercapto, $(C_1-C_6)$ alkylthio, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl, mercapto$(C_1-C_6)$alkyl, or carboxy $(C_1-C_6)$alkyl, lower alkyl substituted by carbamoyl, mono$((C_1-C_6)$alkyl)carbamoyl, di$((C_1-C_6)$alkyl)carbamoyl, di$((C_1-C_6)$alkyl)amino, or carboxy-lower alkanoylamino, $R^a$, or a group $BSO_nA$-; or $R^1$ and $R^2$ taken together with the atoms to which they are attached form a 4-, 5-, 6-, or 7-membered saturated or partially unsaturated carbocycle or a 4-, 5-, 6-, or 7-membered saturated or partially unsaturated heterocycle that comprises carbon and one or two heteroaroms selected from O, S, and $NR^d$, wherein $R^d$ is H or $(C_1-C_4)$alkyl;

n is 0, 1 or 2;

B is hydrogen, $(C_1-C_6)$alkyl, phenyl, heterocyclyl, $(C_1-C_6)$alkanoyl, or phenyl-C(=O)—;

A is $(C_1-C_6)$alkylene, $R^a$ is a cycloalkyl, a cycloalkenyl, or a non-aromatic heterocyclic ring containing up to 3 heteroatoms, any of which may be (i) substituted by one or more substituents selected from $(C_1-C_6)$alkyl, $(C_2-C_6)$alkenyl, halo, cyano, carboxy, —$CO_2R^b$, —$CONH_2$, —$CONHR^b$, —$CON(R^b)_2$, —OH, —$OR^b$, oxo, —SH, —$SR^b$, —$NHCOR^b$, and $NHCO_2R^b$; or (ii) fused to a cycloalkyl or heterocyclic ring;

$R^b$ is $(C_1-C_6)$alkyl or benzyl;

$R_2$ is $(C_1-C_{12})$alkyl, $(C_2-C_{12})$alkenyl, $(C_2-C_{12})$alkynyl, phenyl$(C_1-C_6)$alkyl-, heteroaryl$(C_1-C_6)$alkyl-, phenyl$(C_2-C_6)$alkenyl-, heteroaryl$(C_2-C_6)$alkenyl-, phenyl$(C_2-C_6)$alkynyl-, heteroaryl$(C_2-C_6)$alkynyl-, cycloalkyl$(C_1-C_6)$alkyl-, cycloalkyl$(C_2-C_6)$alkenyl-, cycloalkyl$(C_2-C_6)$alkynyl-, cycloalkenyl$(C_1-C_6)$alkyl-, cycloalkenyl$(C_2-C_6)$alkenyl-, cycloalkenyl$(C_2-C_6)$alkynyl-, phenyl$(C_1-C_6)$alkyl-O$(C_1-C_6)$alkyl-, or heteroaryl$(C_1-C_6)$alkyl-O—$(C_1-C_6)$alkyl- any one of which may be optionally substituted by $(C_1-C_6)$alkyl, $(C_1-C_6)$alkoxy, halo, cyano, phenyl, or phenyl that is optionally substituted by $(C_1-C_6)$alkyl, $(C_1-C_6)$alkoxy, halo, or cyano;

$R_3$ is the characterizing group of a natural or a non-natural α-amino acid in which any functional groups may be protected;

$R_4$ is an ester or thioester group, or a pharmaceutically acceptable salt, hydrate or solvate thereof; and Z is a metal (such as —Zn) binding group selected from —CONHOH, —$COOR^c$, —$CONHOR^c$, —$CONR^cOH$, —$CONHS(O)_2R^c$, —$CONH_2$, —$CONHR^c$, and —$P(O)(OH)_2$, wherein $R^c$ is $(C_1-C_4)$alkyl, aryl$(C_1-C_4)$alkyl-, or heteroaryl$(C_1-C_4)$alkyl-;

wherein any phenyl or heterocyclyl of $R_1$ is optionally substituted with up to four substituents, each of which independently may be selected from $(C_1-C_6)$alkyl, $(C_1-C_6)$alkoxy, hydroxy, mercapto, $(C_1-C_6)$alkylthio, amino, halo, nitro, trifluoromethyl, —COOH, —$CONH_2$, cyano, —$COOR^A$, —$COONHR^A$ or —$COONR^AR^A$ wherein $R^A$ is a $(C_1-C_6)$alkyl group or the residue of a natural alpha-amino acid.

In one embodiment the invention provides a method for producing analgesia in an animal comprising administering to the animal 1) a compound of formula (I) or a pharmaceutically acceptable salt thereof, and 2) a therapeutic agent. In another embodiment the invention provides a a pharmaceutical composition, comprising 1) a compound of formula (I) or a pharmaceutically acceptable salt thereof, 2) a therapeutic agent, and 3) an excipient. Therapeutic agents that can be administered according to the methods of the invention or that can be included in compositions of the invention include:

Opioids, such as morphine,

Non steroidal anti-inflammatory drugs (NSAIDs), including non-selective Cyclooxygenase (COX) inhibitors, such as ibuprofen, and selective COX-2 inhibitors, such as celecoxib, Antidepressants including:
Tricyclic and tetracyclic antidepressants (TCAs), such as imipramine,
Selective serotonin reuptake inhibitors (SSRI), such as fluoxetine,
Serotonin-noradrenaline reuptake inhibitors (SNRI), such as venlafaxine,
Noradrenaline reuptake inhibitors (NRI), such as reboxetine,
Serotonin (5-HT2) antagonists and reuptake inhibitors (SARI), such as trazodone,
Noradrenergic and specific serotonergic antidepressive agents (NaSSA), such as mirtazapine,
Reversible inhibitors of monoaminoxidase A (rMAO-A), such as moclobemide, Anticonvulsants, such as carbamazepine and gabapentin,
Corticosteroids, such as hydrocortisone,
N-Methyl-D-Aspartate (NMDA) receptor antagonists, such as ketamine and methadone,
Adrenergic pathway modifiers, such as clonidine,
Antispasmodics, such as hyoscine, and
Membrane stabilizing drugs, such as lidocaine and flecanide.

The invention will now be illustrated by the following non-limiting Examples.

EXAMPLES

The compound tosedostat is commercially available and can be prepared as described in International Patent Application Publication Number WO1999/046241 and U.S. Pat. Nos. 6,169,075 and 6,462,023.

Example 1. Evaluation of Analgesic Activity of Tosedostat

Human immune cells release certain opioid receptor peptides such as endorphins (ENDs), enkephalins (ENKs), and dynorphins (DYNs) in response to stressful stimuli. These peptides stimulate the opioid receptors providing euphoria and a feeling of relief to the body under stressful stimuli. These neuropeptides (ENDs, ENKs, and DYNs) are usually digested by various peptidases. Response to thermally induced pain was measured in animal models by using Hot-Plate Test, and with Tail-Flick Analgesia Meter.

Hot-Plate Test:

Analgesic potencies of control and test compounds were determined in male CF1 mice using the hot-plate model. The hot plate was the top surface of an enclosed cylindrical glass bath through which thermostatically controlled hot water was circulated. Under the conditions used, the temperature of the surface of the cylinder was maintained at 55° C. Mice were dosed intraperitoneally (i.p.) or intracerebroventricularly (i.c.v.) with the test compound tosedostat dissolved in 50% DMSO and saline solution. At various time points post-injection (15, 30, 45, 60, 75, and 90 min), mice were placed on the hot surface and the time recorded when mice either exhibited hind-paw shake/lift, hind-paw lick, or jumped off of the platform as their reaction times. Reaction times were also determined twice for each mouse at 15-min intervals half an hour before injecting the drug to establish a baseline reaction time control value. Mice having a mean reaction time greater than 13 seconds were excluded as non-responders. For animals which did not leave the hot surface, a cut-off time of 30 seconds was used to avoid injury to the tissue of the animals. The observed analgesic effects are presented as the percentage maximum possible effect (% MPE) calculated by % MPE=(Test−Baseline)/(Cutoff−Baseline)×100, where Test is the observed latency to respond after the treatment, Baseline is the latency to respond prior to the treatment, and Cutoff is the time at which the test is ended in the absence of a response from the animal—30 seconds for these experiments.

FIG. 1 shows the analgesic evaluation of tosedostat at a single time-point, 15 minutes after injection of the test compound. Tosedostat was dissolved in 50% solution of DMSO in saline. For intracerebroventricular administration of the compound, dosage of 100 µg was tested. For intraperitoneal administration, dosage of 58.1 mg/Kg was evaluated. This preliminary experiment revealed a nominal analgesic effect for the group with i.c.v. route of administration. However, the group with intraperitoneal administration of the compound revealed more than two-fold mean latency indicating a significant analgesic effect of the compound.

Figure 2A:
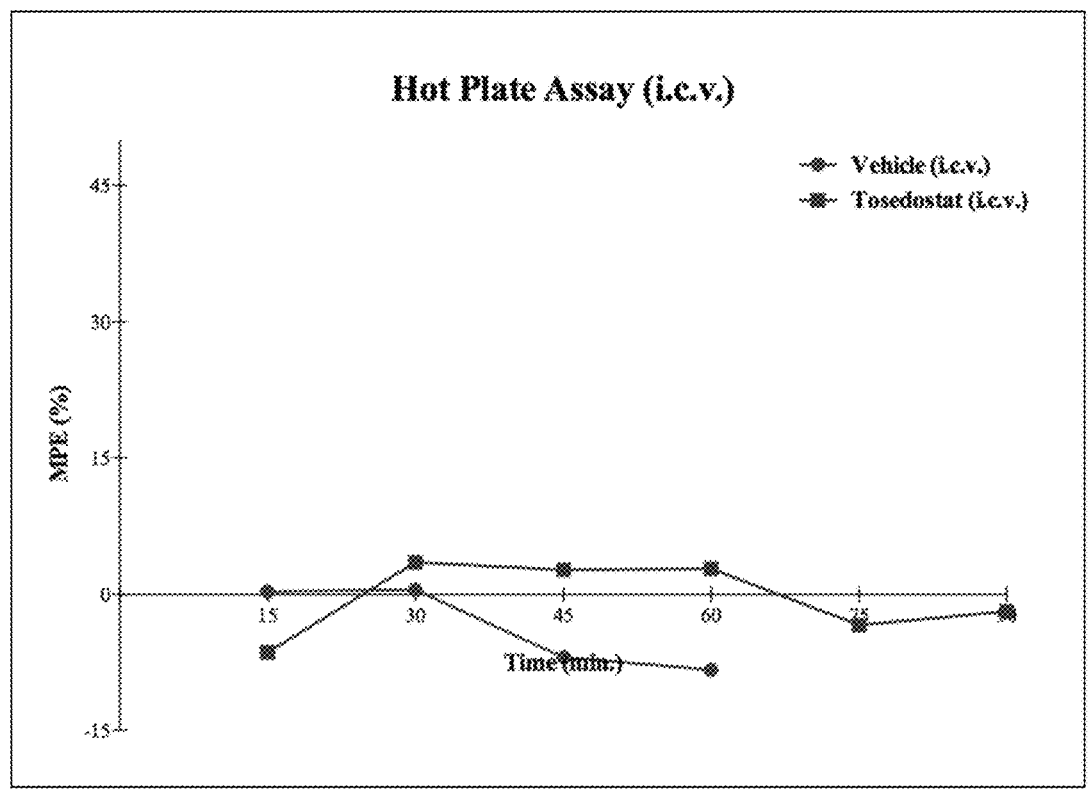
FIGS. 2A-2B illustrate the analgesic potency of tosedostat in Hot-Plate assay. The test compound was dissolved in 50% saline in DMSO solution. (2A) Route of administration: i.c.v.; dosage: 100 μg per mouse (2B) Route of administration: i.p.; dosage: 58.1 mg/Kg each mouse. See Example 1.
Figure 2B:
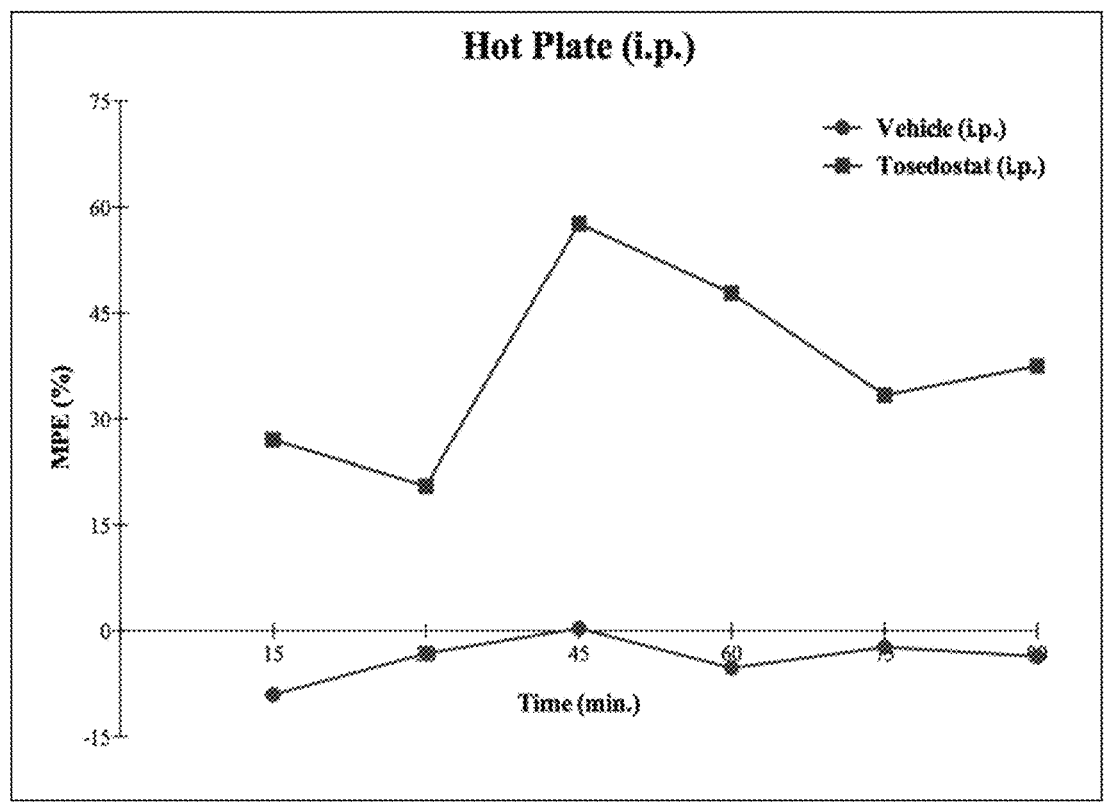

FIGS. 2A-2B shows data collected for time points 15, 30, 45, 60, 75, and 90 minutes after injection of the test compound. These data corroborate the observations made in the single time-point study where the test compound administered intracerebroventricularly did not show analgesic effect (FIG. 2a), while for the animal group injected intraperitoneally, a significant analgesic effect was observed with maximum effect observed from 45 to 60 minutes post injection (FIG. 2b).

Tail-Flick Model:

The Tail-Flick test comprises of acute nociception in which the tail of the test animal is thermally stimulated. The time it takes for the animal to either flick or withdraw its tail is recorded as a measure of the response to the thermal stimuli. For this test, mice were gently restrained in a cloth; the tail-flick beam was centered on the dorsal surface of the tail (about 15 mm from the end of the tail). The heat source was activated, and the latency for withdrawal of the tail was recorded. The intensity of the tail-flick beam was adjusted so that the average withdrawal time of the baseline measurement was 2 to 4 sec. For each animal, a baseline response latency was determined in two consecutive responses measured at 5 minute intervals. Animals were tested at 15, 30, 45, 60, 75, and 90 minutes after drug administration. To protect against tissue injury, the test was terminated after 10 seconds if the animal did not withdraw its tail.

Figure 3A:
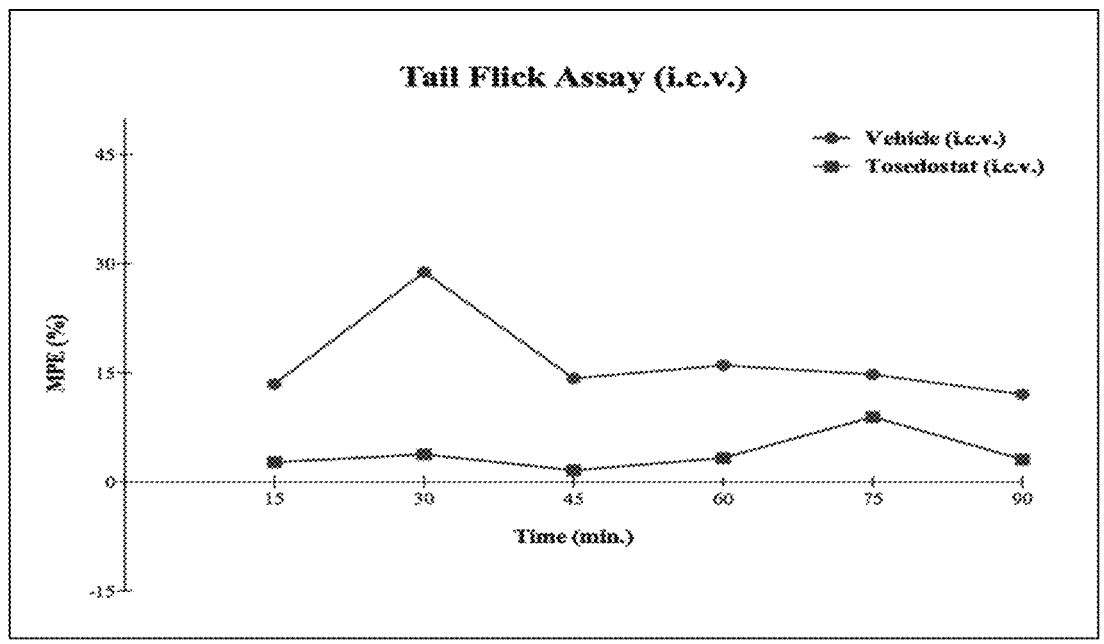
FIGS. 3A-3B illustrate the analgesic potency of tosedostat in Tail-Flick assay. The test compound was dissolved in 50% saline in DMSO solution. (3A) Route of administration: i.c.v.; dosage: 100 μg per mouse (3B) Route of administration: i.p.; dosage: 58.1 mg/Kg of each mouse. See Example 1.
Figure 3B:
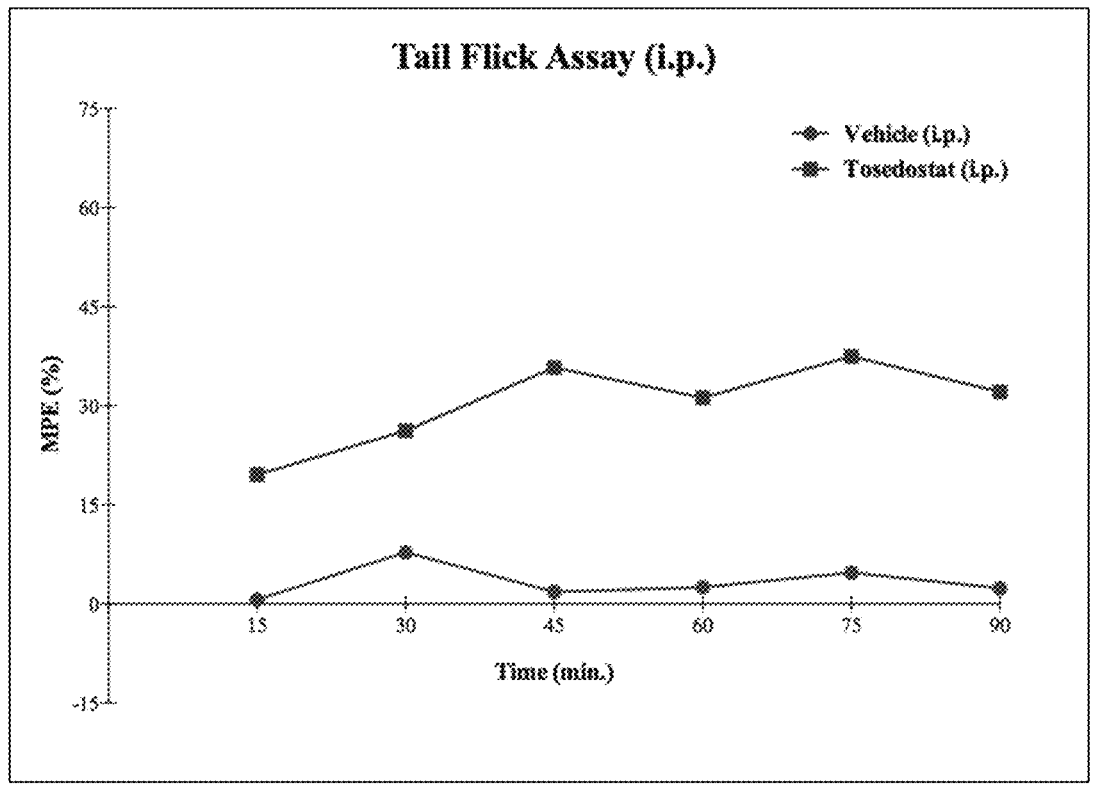

Tail-flick experiments corroborated the findings from the hot-plate assay. FIG. 3a shows that tosedostat does not impart analgesic effect when administered directly to the brain. Intraperitoneally administered tosedostat displayed a seven-fold increase in the analgesic response over the course of the 90 minutes of the experiment, as shown in FIG. 3b.

Tail-flick assay represents pain-response of the central nervous system at a distinctive level compared to the pain-response generated in the hot-plate test. While hot-plate method is more sensitive at supraspinal level, the tail-flick method mostly embodies a spinal response to the noxious stimuli. A comparison of results from the two analgesic study models for intraperitoneally administered test compound revealed a milder response for the tail-flick experiment. The hot-plate experiments recorded about two-fold better analgesic response over the course of 90 minute experiments as compared to the response recorded in tail-flick experiments—compare FIGS. 2b and 3b.

Example 2. Evaluation of Tosedostat Distribution

Figure 4:
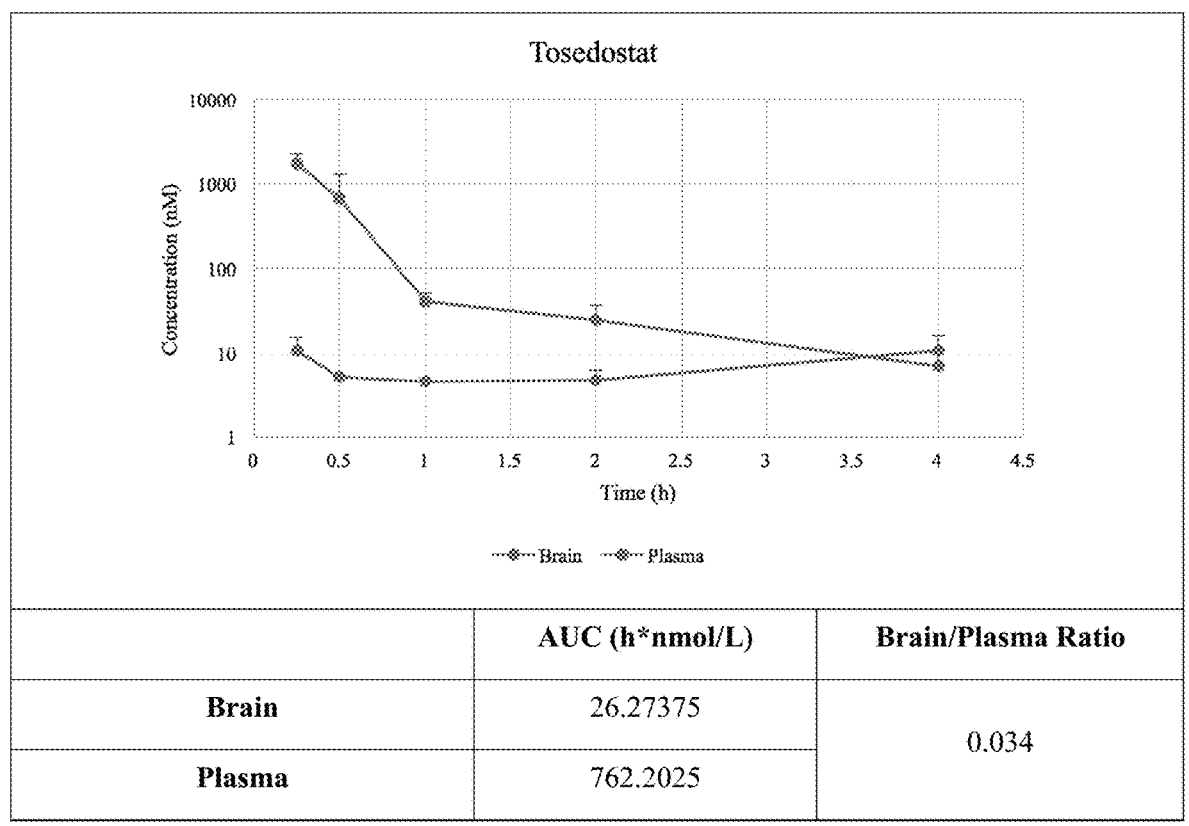
FIG. 4 illustrates the pharmacokinetic distribution of tosedostat in brain and plasma. Tosedostat was dissolved in 50% saline in DMSO solution. A dosage of 10 mg/Kg was administered intraperitoneally. Brain and plasma samples were harvested and analyzed via LC-MS/MS for the presence of tosedostat over a period of 4 hours. AUC: Area Under Curve. See Example 2.

To ascertain the distribution of tosedostat in a subject's body, plasma and brain samples were harvested from intraperitoneally treated animal groups and analyzed via LC-MS/MS (FIG. 4). These pharmacokinetic experiments showed minimal presence of tosedostat in the brain homogenate samples as compared to the plasma samples.

Figure 5A:
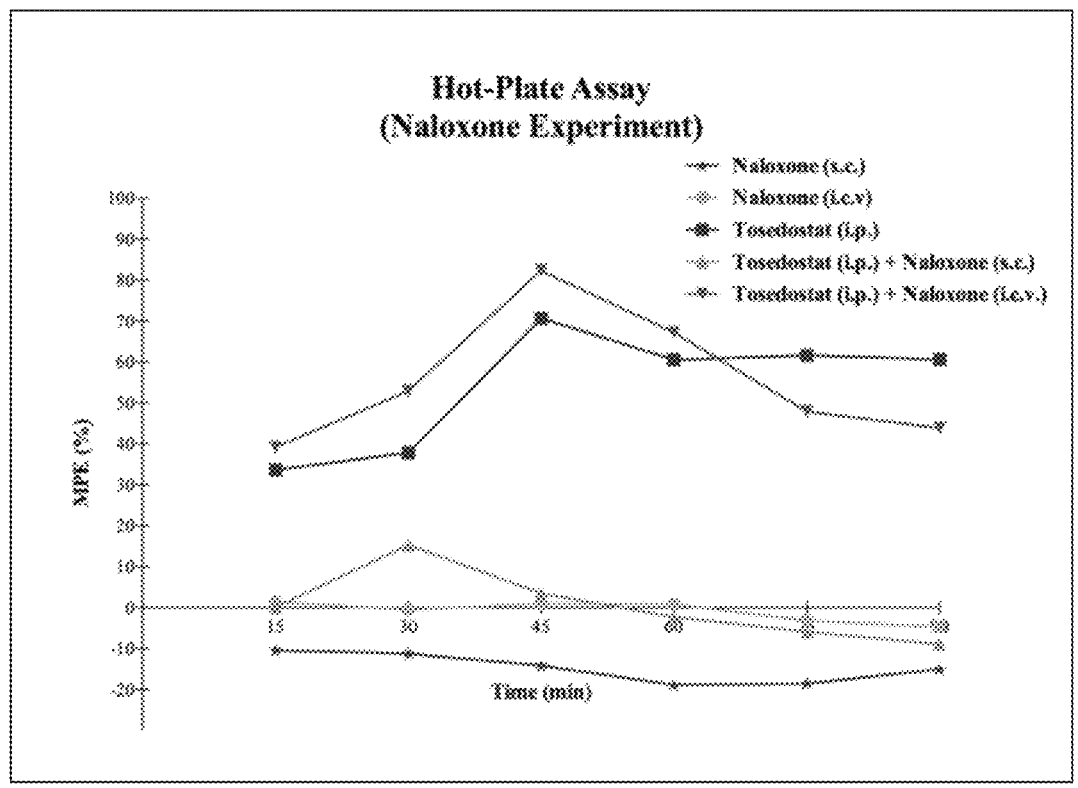
FIGS. 5A-5B. Tosedostat (58.1 mg/Kg) was dissolved in 50% saline in DMSO solution and administered intraperitoneally. Naloxone dissolved in saline, was administered subcutaneously (5 mg/Kg) or intracerebroventricularly (5 μg per mouse). See Example 3.
Figure 5B:
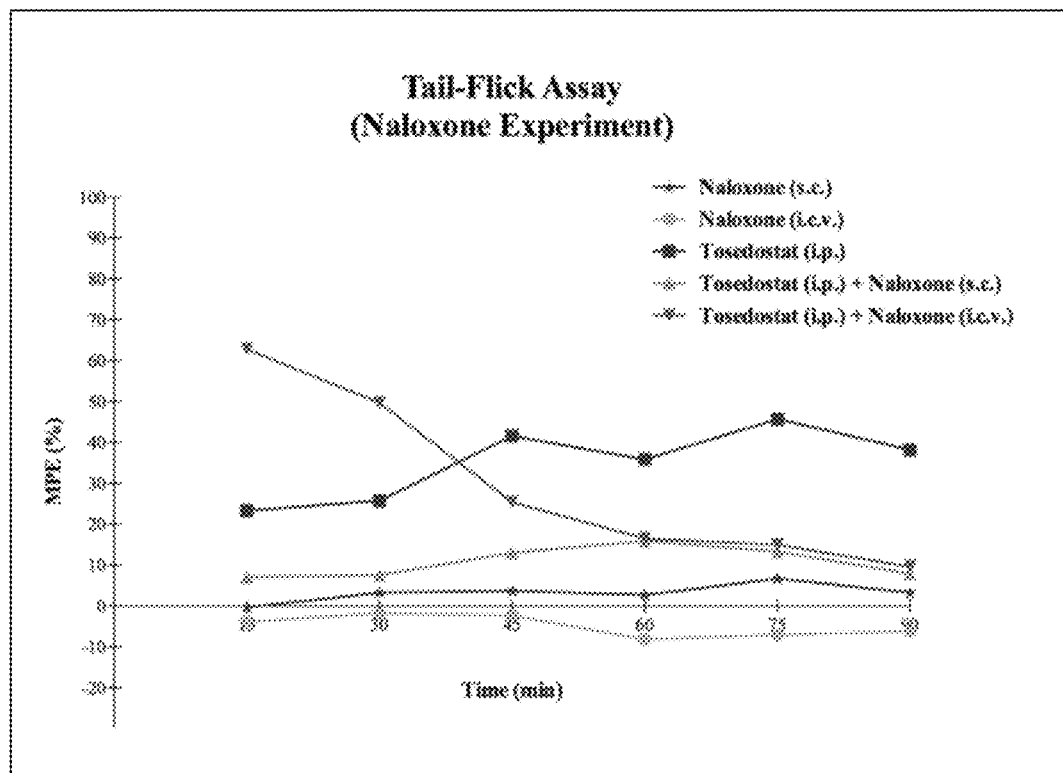

Example 3. Analgesic Potency of Intraperitoneally Administered Tosedostat Along with the Administration of Opioid Receptor Antagonist Naloxone Effects of opiate antagonist naloxone were studied by administering it along with tosedostat. Tosedostat (58.1 mg/Kg) was dissolved in 50% saline in DMSO solution and administered intraperitoneally. Naloxone dissolved in saline was either administered subcutaneously (s.c.; dosage: 5 mg/Kg) via an injection to the interscapular skin, or it was given intracerebroventricularly (5 µg per mouse). FIGS. 5a and 5b show that while administration of tosedostat triggered a nociceptive response, the naloxone only animal groups (both s.c., and i.c.v) had no effect on latency. Subcutaneously administered naloxone blocked the analgesic action of tosedostat. Interestingly, no attenuation of analgesic response was observed in animals with centrally administered naloxone. These results strongly indicate that the pain-relieving property of tosedostat is a periphery driven phenomenon rather than originating from the brain. Expectedly, the analgesic potency of test compounds was observed to be of lesser magnitude in tail-flick as compared to the hot-plate model. However, similar trends were observed in both the experimental pain models.

Figure 6A:
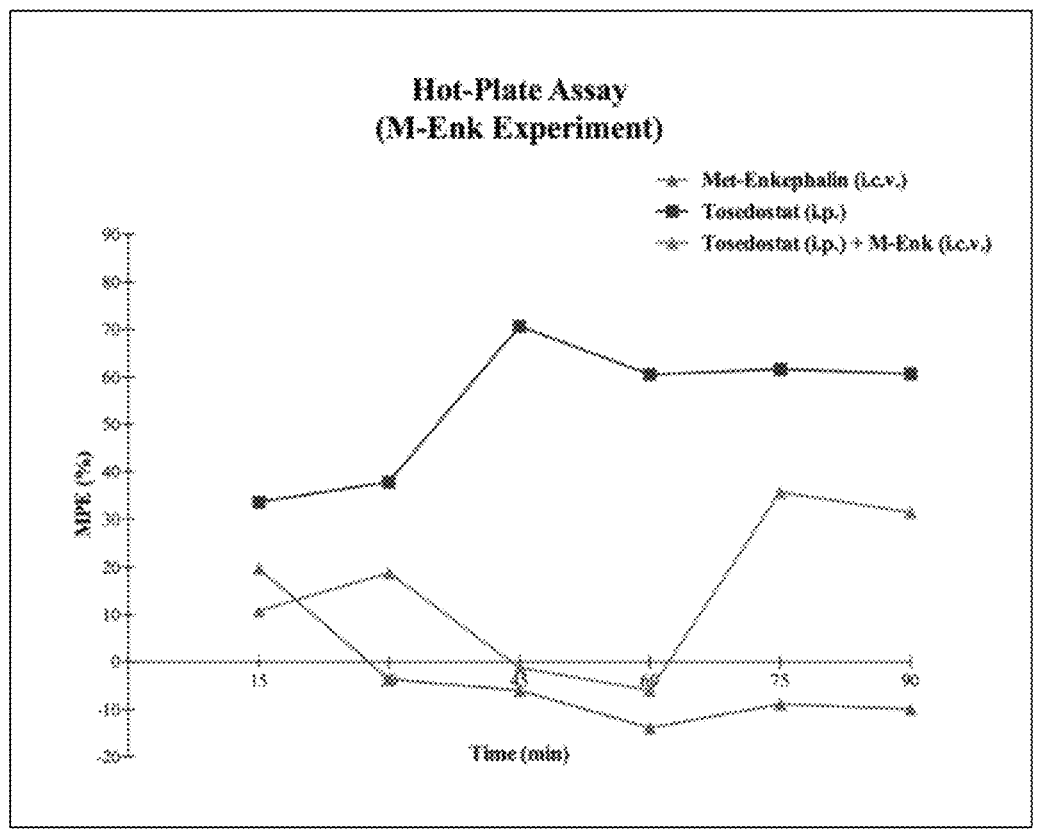
FIGS. 6A-6B shows the analgesic potency of intraperitoneally administered tosedostat along with intracerebroventricularly administered neuropeptide Met-Enkephalin in both hot-plate and tail-flick assays. The test compounds were dissolved in 50% saline in DMSO solution Tosedostat (58.1 mg/Kg) was administered intraperitoneally. M-enkephalin (50 μg) was administered intracerebroventricularly. See Example 4.
Figure 6B:
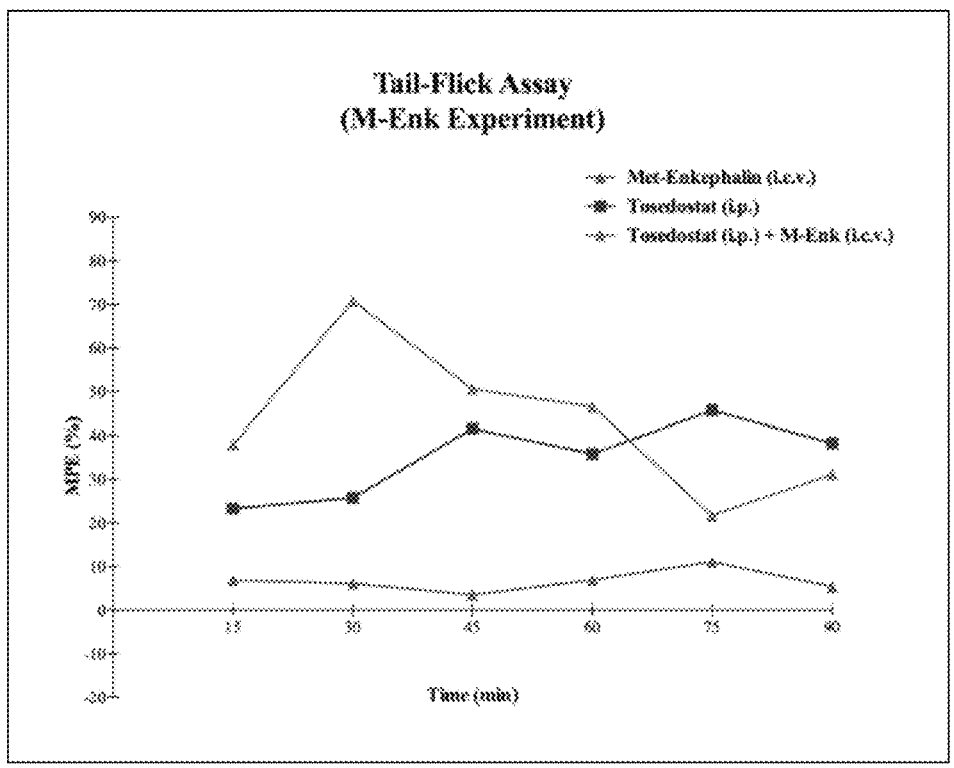

Example 4. Analgesic Potency of Intraperitoneally Administered Tosedostat Along with Intracerebroventricularly Administered Neuropeptide Met-Enkephalin While protecting the endogenous opioid receptor ligand Met-Enkephalin (M-Enk) from various peptidases is the more promising approach, the effects of stimulating the opioid system by increasing local concentration of enkephalins has also been studied. FIGS. 6a and 6b depict the effects of intracerebroventricular administration of extracellular M-Enk. Met-Enk administered by itself did not prompt a significant analgesic response, presumably due to its metabolism by the peptidases.

Example 5. Comparison of Tosedostat with Thiorphan

Figure 7:
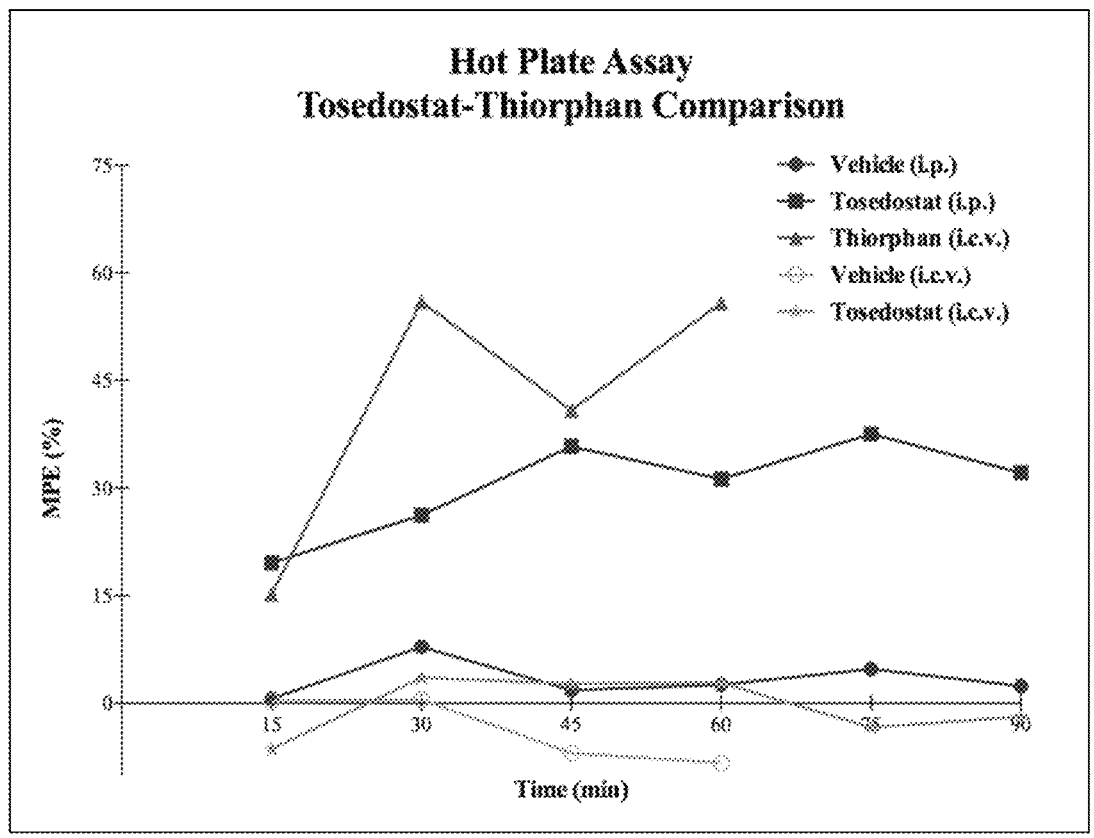
FIG. 7 shows a comparison of analgesic potency of tosedostat with thiorphan in a hot-plate model. Tosedostat was dissolved in 50% saline in DMSO solution. For i.c.v. administration, the amount of tosedostat injected: 100 μg per mouse. For i.p. route of administration, dosage of tosedostat tested: 58.1 mg/Kg per mouse. Dosage of thiorphan tested: 50 μg per mouse administered intracerebroventricularly. Thiorphan was not administered intraperitoneally. See Example 5.

Thiorphan is a known aminopeptidase inhibitor with Antinociceptive properties. A comparison of analgesic effect of thiorphan with tosedostat in the hot-plate model is presented in FIG. 7.

Example 6. Tosedostat as an Analgesic Agent

Tosedostat is a clinical candidate being evaluated for its oral efficacy in the treatment of hematological malignancies as well as solid tumors.

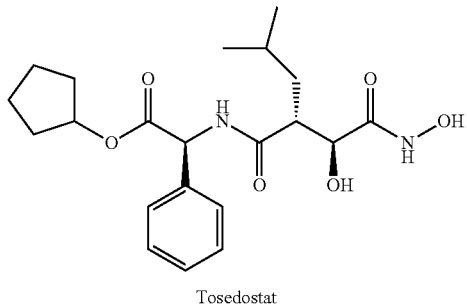 [SMILES: CC(C)C[C@@H](C(=O)N[C@H](C(=O)OC1CCCC1)c1ccccc1)[C@H](O)C(=O)NO]

Tosedostat

The pharmacological activity of the molecule against cancer is attributed to its propensity to effectively inhibit various aminopeptidases. Several of these aminopeptidases are responsible for cleavage of short-chain peptides into amino acids. Impeding the function of these peptidases creates nutrient stress in cells by disrupting the supply of recycled amino acids for protein synthesis. The mechanism termed Amino Acid Deprivation Response (AADR) presents a remarkable pre-erence for transformed cells as compared to healthy cells making it a highly valuable approach towards cancer therapy. Inspired by the anti-proliferative effects displayed by matrix metalloproteinase inhibitor batimastat, Krige et al. presented their studies with tosedostat as a viable anti-cancer agent. Among various metalloenzymes described, aminopeptidases became the enzymes of focus because of the well-studied analogous antiproliferative effect exerted by aminopeptidase inhibitor bestatin. Aminopeptidase N (APN, EC 3.4.11.2) was listed as one of the major enzymes amongst the aminopeptidases of interest by Krige and coworkers.

Figure 9:
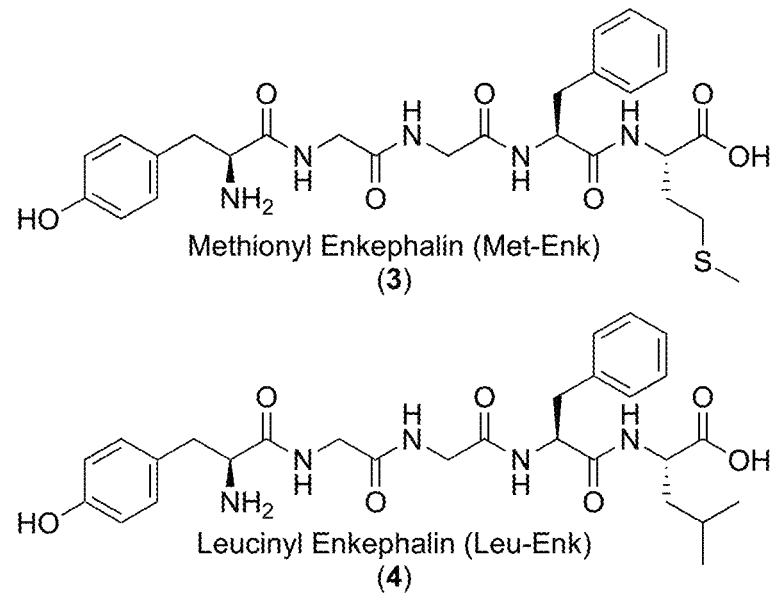
FIG. 9. Various endogenous neuropeptides including Met-Enkephalin (3) and Leu-Enkephalin (4)

Apart from the implications in intracellular peptide degradation, APN is also known to participate in the hydrolysis of endogenous neuropeptides. Among these neuropeptides (FIG. 9), enkephalins have garnered particular interest owing to their noteworthy role in the nociceptive system in the body. Encoded by the gene proenkephalin (PENK), Methionyl Enkephalin (Met-Enk) and Leucinyl Enkephalin (Leu-Enk), have been studied for their analgesic properties in various models of pain, both neuropathic and inflammatory. These penta-peptide ligands of the opioid receptors are known to interact with both the δ-opioid receptors (DORs) and the μ-opioid receptors (MORs). Konig et al reported behavioral studies with PENK knock-out mice. Hyperalgesic response to painful stimuli as recorded for these mice deficient in enkephalins, attested to their indispensable function in biological pain-response.

Currently, steroidal and non-steroidal anti-inflammatory drugs are described but they suffer from serious side-effects such as ulcers, hypersensitivity, bleeding, and major organ toxicity (especially, kidney and liver). Using combination therapy with other opiates or adrenergic agonists also have respiratory depression and sedative side effects and thus, low patient compliance. More importantly, these options have a high abuse potential and often lead to increase in tolerance, dependency, and addiction. Enkephalins provide several advantages over the use of exogenous painkillers currently in use for alleviation of pain. Since the release of enkephalins is homeostatically regulated by the patient's body, the opioid receptors do not undergo overstimulation thus avoiding behavioral issues observed with the use of exogenous opioid receptor stimulants as mentioned above. However, these endogenous neuropeptides are highly susceptible to rapid digestion due to the enzymatic action of various peptidases. Indeed, half-life times for both enkephalins have been found to be as short as 11 minutes. Introducing inhibitors of enzymes responsible for the digestion of enkephalins would provide analgesic effect by permitting these natural analgesics to exist for longer period of time than they would normally exist and consequently allow them to provide a stronger and prolonged analgesic relief.

In vivo studies were conducted in order to determine the analgesic effect produced by the anti-cancer clinical candidate tosedostat. Various modes of administration for the drug candidate were studied. The experiments showed that the molecule acts on the peripheral nociceptive system thus providing an attractive avenue for the exploration of alternatives to the conventional opioid receptor stimulants.

Results and Discussion

Figure 10:
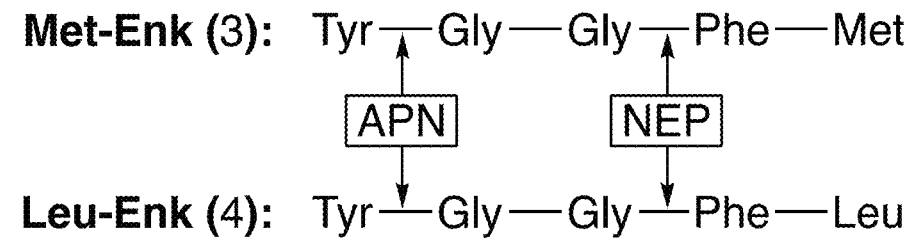
FIG. 10. Cleavage sites for APN and NEP on Met-Enk (3) and Leu-Enk (4).

Roques and coworkers reported detailed studies on the analgesic effect produced by prolonging the life of these endogenous neuropeptides. Early investigations revealed that inhibition of degradation of one enzyme does not inhibit the degradation of enkephalins enough to produce any significant analgesia. Several studies simultaneously targeting more than one enzyme involved in breakdown of enkephalins were reported. Roques et al have named their dual inhibitors DENKIs (Dual ENKephalinase Inhibitors). Some of these inhibitors have advanced to the stage of clinical evaluation for their nociceptive effects. DENKIs have focused on the inhibition of action of aminopeptidase N (APN) and neprilysin (NEP, EC 3.4.24.11). Both the enzymes are zinc-dependent metallopeptidases, and have concurrent topological distribution. Both are membrane anchored ectoenzymes. Encoded by the ANPEP gene, APN is an exopeptidase that is responsible for the release of neutral or basic amino acids from the N-terminal of the peptides. NEP is an endopeptidase known for preferential cleavage of peptides between hydrophobic amino acid residues, especially with phenylalanine or tyrosine at the P1' position. Correspondingly, APN cleaves the N-terminal Tyr for both Met-Enk and Leu-Enk while NEP cleaves between Gly-Phe bond of both the penta-peptides (FIG. 10).

Figure 8:
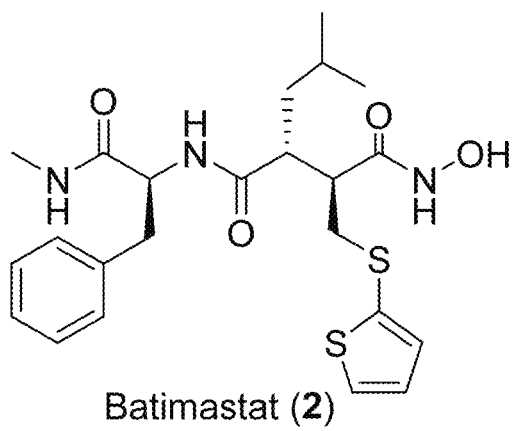
FIG. 8. Batimastat.

Potency of tosedostat was determined against the two enzymes of note, APN and NEP and compared with bestatin, thiorphan, and batimastat (FIG. 8). After initial testing at single concentration (10 μM), dose response curves to determine the $IC_{50}$ values were obtained (Table 1).

TABLE 1

|  | APN | | NEP | |
|---|---|---|---|---|
|  | @ 10 µM | IC$_{50}$ (µM) | @ 10 µM | IC$_{50}$ (µM) |
| Tosedostat (1) | 83% | 0.933 | 79% | 0.9 ± 0.23 |
| Batimastat (2) | — | 0.2117 | 60% | 4.476 |
| Bestatin | 77.6% | 0.796 | 0% | >100 |
| Thiorphan | 0% | >100 | 90% | 0.008 ± 0.27 |

Results from the biochemical assay against APN corroborated the information reported in the literature for the activity of the tested compounds. Bestatin maintained its specificity in inhibiting only APN with no activity against NEP. Analogous to the specificity of bestatin against APN, thiorphan, expectedly, inhibited only NEP with showing no activity against APN. Tosedostat showed micromolar activity against APN. Interestingly, it also inhibited NEP with IC$_{50}$ value of 0.9 µM. Batimastat was also found to inhibit both APN and NEP. Encouraged by these data, the implications of tosedostat in the nociceptive pain-response system was evaluated. In vivo studies to assess pharmacological effects of tosedostat in models of both acute pain (hot-plate, and tail-flick assays), and persistent pain (formalin, and acetic acid writhing tests) were conducted.

Antinociceptive Behavioral Test for Acute Pain: Hot-Plate Model

Figure 11:
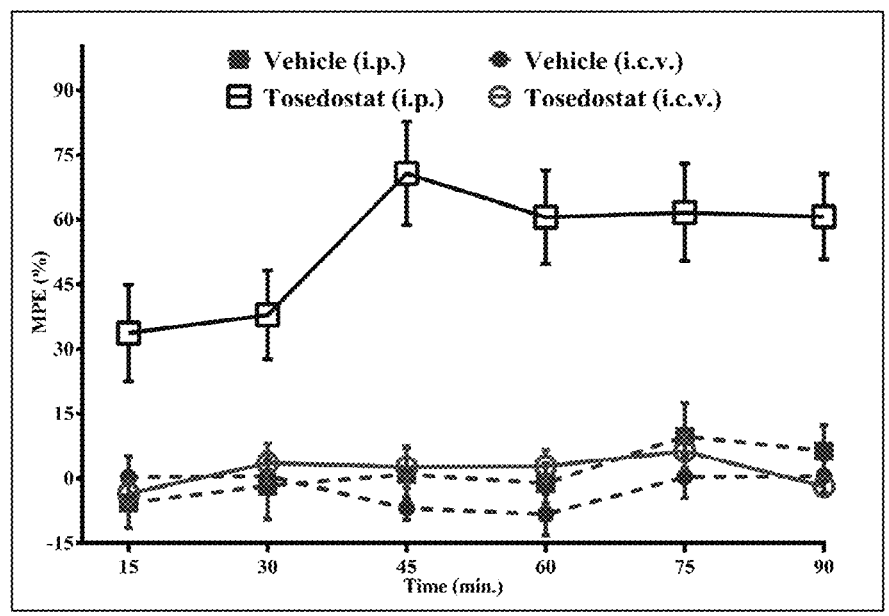
FIG. 11. Evaluation of time-dependent antinociceptive effects of tosedostat in mouse hot-plate assay. The test compound was dissolved in 50% saline in DMSO solution. Comparison of intraperitoneally delivered tosedostat (□) and vehicle control (■), with intracerebroventricularly administered tosedostat (○) and vehicle control (●). The y-axis represents the effect of the dose expressed in percentage of maximum possible effect (% MPE). Error bars represent ±SEM for each time-point. For tosedostat, n=8-14 animals/time-point). Dosage for i.c.v. injection=100 μg per mouse. Dosage for i.p. delivery=58.1 mg/Kg each mouse.

In this transient pain model, a thermal analgesiometer hot-plate was utilized for the determination of antinociceptive potency of test compounds against acute thermal stimulus. Mice were administered compounds via intraperitoneal (i.p.) or intracerebroventricular (i.c.v.) routes. Data were collected for 15, 30, 45, 60, 75, and 90 minute timepoints after injection of the test compounds (FIG. 11). These data corroborate the observations made in the single time-point study where the test compound administered intracerebroventricularly displayed nominal analgesic effect. Observation of a significant analgesic effect in the animal group injected intraperitoneally was replicated in the extended experiment. The time period for observed maximum analgesic response was identified to be 45 to 60 minutes post injection. The results are expressed as a percent of the maximum possible effect (% MPE) according to the equation:

$$\% \text{ MPE} = [(\text{Post-drug latency} - \text{Pre-drug latency})/(\text{Cut-off} - \text{Pre-drug latency})] \times 100.$$

Systemic administration of tosedostat produced significant time-dependent anti-nociception with maximum effect observed at 45 minutes post injection. In contrast, centrally delivered tosedostat did not register substantial analgesic outcome. At 45 minutes time-point, a potency ratio of approximately 35:1 was observed for tosedostat delivered to mouse peritoneum as compared to intracerebroventricularly administered dosage.

Antinociceptive Behavioral Test for Acute Pain: Tail-Flick Assay

Figure 12:
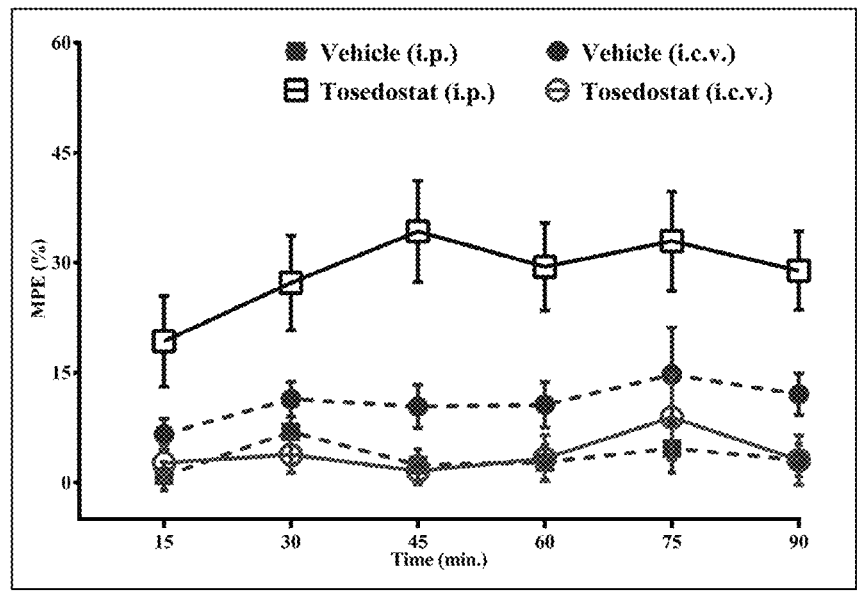
FIG. 12. Antinociceptive effects of tosedostat in mouse tail-flick assay. The test compound was dissolved in 50% saline in DMSO solution. Comparison of intraperitoneally delivered tosedostat (□) and vehicle control (■), with intracerebroventricularly administered tosedostat (○) and vehicle control (●). The y-axis represents the effect of the dose expressed in percentage of maximum possible effect (% MPE). Error bars represent ±SEM for each time-point with n≥12 animals/time-point. Dosage for i.c.v. administration=100 μg per mouse. Dosage for i.p. delivery=58.1 mg/Kg each mouse.

The tail-flick model represents another test of response thresholds to thermally induced high-intensity transient pain stimuli. While hot-plate method is more sensitive at supraspinal level, the tail-flick method mostly embodies a spinal reflex response to noxious stimuli. The test comprises of acute nociception in which the tail of the test animal is thermally stimulated. The time it takes for the animal to either flick or withdraw its tail is recorded as a measure of the response to the stimuli. Animals were tested at 15, 30, 45, 60, 75, and 90 minutes after drug administration. Tail-flick experiments corroborated the findings from the hot-plate assay. FIG. 12 shows that tosedostat does not prompt a potent analgesic effect when administered directly to the brain. In comparison, systemically delivered tosedostat displayed a seven-fold potentiation in the analgesic response over the course of the 90 minutes of the experiment. Furthermore, the hot-plate experiments recorded about two-fold better analgesic response over the course of 90 minute experiments as compared to the response recorded in tail-flick experiments.

Antinociceptive Behavioral Test for Persistent Pain: Acetic Acid Writhing Test

Figure 13:
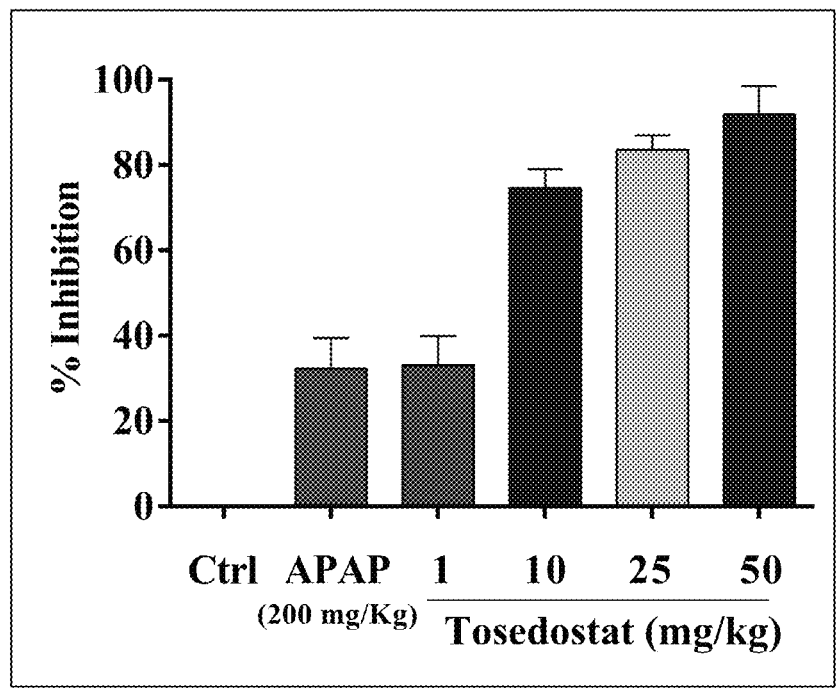
FIG. 13. Evaluation of analgesic potency of tosedostat in acetic acid mouse writhing assay. Tosedostat was dissolved in 50% saline in DMSO solution. APAP was dissolved in saline. Both test compounds were delivered intraperitoneally. Number of writhing episodes in 30-minute period beginning at the acetic acid delivery were counted. Data are expressed as means. Error bars represent ±SEM. N=3-8 animals for the reported dosages.

Acetic acid writhing test embodies a chemically induced persistent pain model for the determination of analgesic effect of test compounds. Acclimatized animals are treated systemically with a dilute solution of acetic acid inducing abdominal constrictions (writhes) or extension of hind limbs in the animal. The writhes and extensions are counted within a predetermined period of time to analyze the efficacy of the test compound. The results are expressed as percent inhibition of acetic acid induced writhes in 30 minutes (FIG. 13). Percent inhibition is calculated according to the equation:

$$\% \text{ Inhibition} = [(\text{Mean number of writhes for control} - \text{Mean number of writhes for test compound})/(\text{Mean number of writhes for control})] \times 100.$$

Tosedostat treated groups displayed significant attenuation of writhing episodes in a dose-dependent manner as compared to the control groups. Comparison with acetyl-para-aminophenol (APAP, acetaminophen) as positive control, underscores the significantly stronger analgesic response achieved by tosedostat in this peripheral pain model. A dosage of only 1 mg/Kg of tosedostat was required to achieve analgesic effect equivalent to the activity observed with 200 mg/Kg for APAP. A 50 mg/Kg dosage of tosedostat inhibited >90% of writhings, attesting to the efficacy of this peptidases' inhibitor in exerting an analgesic effect. The potent analgesic effect displayed by tosedostat is especially noteworthy since acetic acid writhing assay is an established method to study the effect of potential analgesic agents on peripheral opioid receptors.

Antinociceptive Behavioral Test for Persistent Pain: Formalin Test

The formalin test is another variant model for analyzing pain-relieving properties of test compounds in pain produced by inflammation or by injury to peripheral tissue. It is divergent from the acetic acid writhing assay in producing a biphasic response. These pharmacologically distinct phases are generally observed from 1 to 10 minutes, and 15 to 60 minutes post injection. While phase-I is caused by a rapid relay response in pain fibers, sensitization due to peripheral inflammation results in phase-II response in this model. Moreover, a comparison with APAP in the same assay showed tosedostat to be significantly advantageous in potency.

Figure 14:
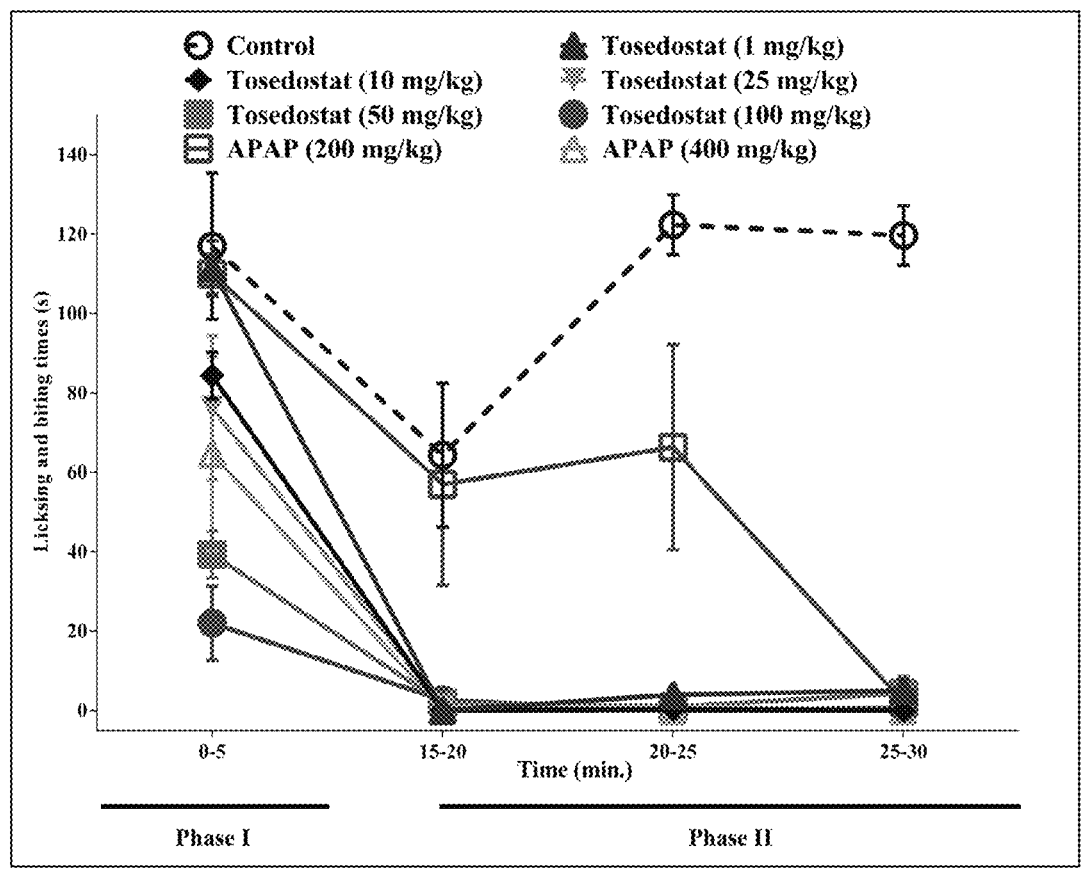
FIG. 14. Evaluation of analgesic potency of tosedostat in formalin assay in mice. The test compounds were dissolved in 50% saline in DMSO solution and delivered systemically. The y-axis represents number of times the animal licked or bit its paws. Error bars represent ±SEM for each time-point with n=3 animals per dose.

Intraperitoneally administered tosedostat displayed a dose-dependent response in phase-I of the experiment (FIG. 14). Interestingly, the phase-II nociceptive action of formalin was found to be completely suppressed even at dosages as low as 1 mg/Kg of tosedostat. These data provide strong evidence in support of the analgesic activity of tosedostat originating from its action at the peripheral antinociceptive system.

Antinociceptive Activity of Tosedostat: Central Vs Peripheral Mechanism

Figure 15:
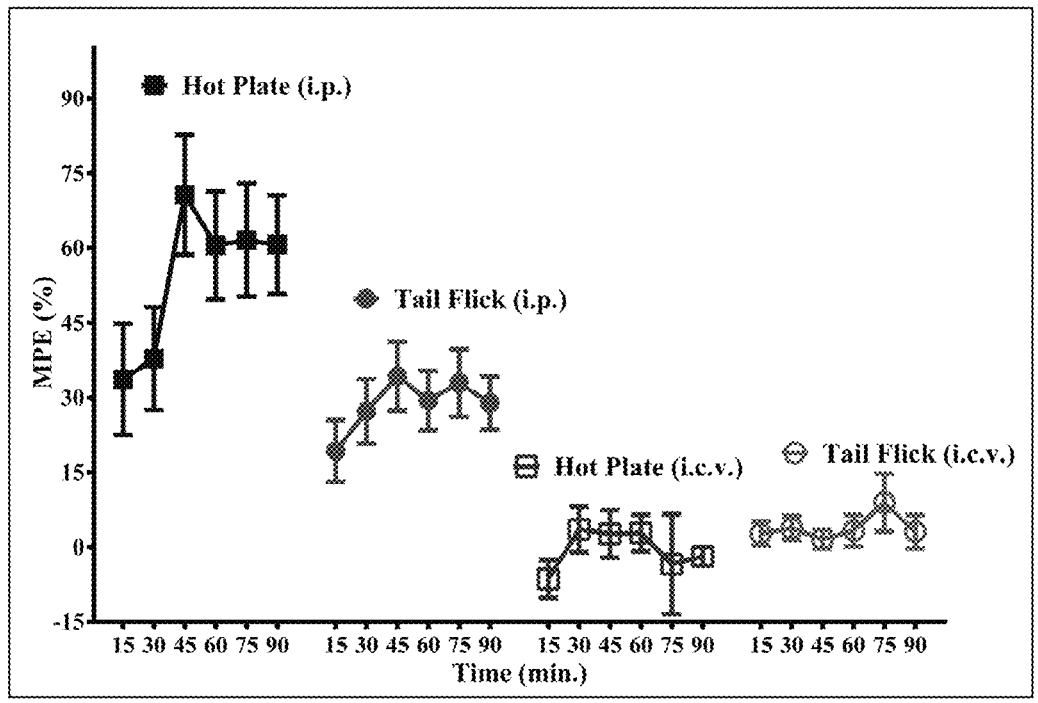
FIG. 15. Grouped graphical representation of relative antinociceptive effect of systemically delivered test compound compared to centrally delivered test compound in mouse hot-plate and tail-flick assays.

To further ascertain the origins of observed analgesic action of tosedostat, the efficacy among various modes of administration of the compound was evaluated. Towards that end, the results from administering the compound intraperitoneally were compared with the results obtained from giving the compound directly to the brain (FIG. 15). Direct administration of tosedostat to the brain was found to be ineffective in furnishing an antinociceptive response. However, intraperitoneal administration of the compound elicited a potent antinociceptive effect in hot-plate assay and a moderate response in tail-flick assay. These data strongly suggest that the analgesic activity of tosedostat is achieved from its action on the peripheral antinociceptive system.

Figure 16:
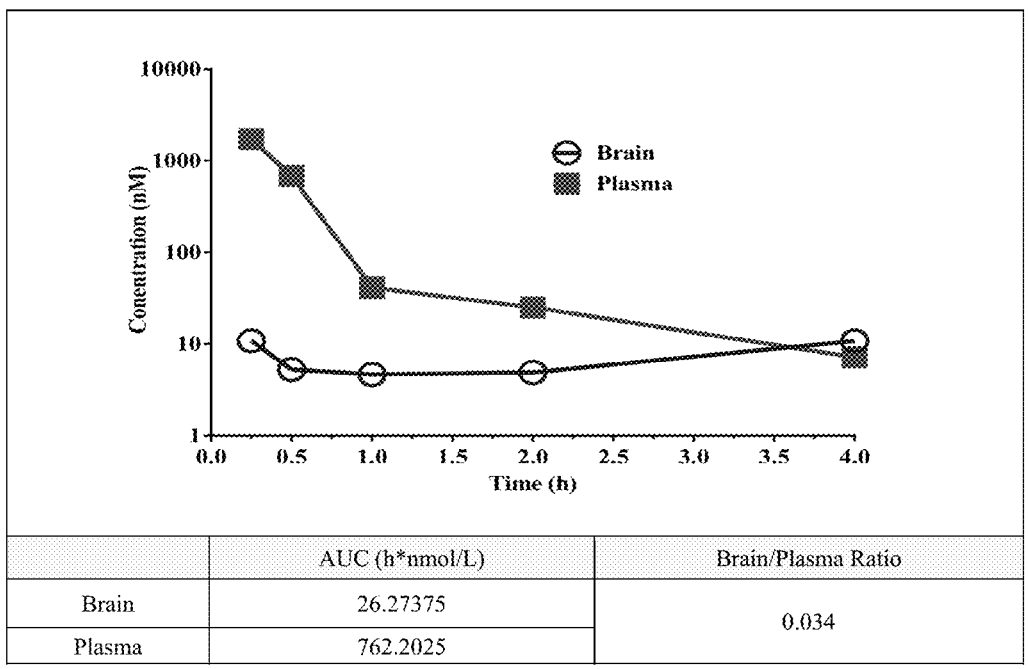
FIG. 16. Distribution of tosedostat in brain and plasma. Tosedostat (10 mg/Kg) was administered intraperitoneally. Brain and plasma samples were harvested and analyzed via LC-MS/MS for the presence of tosedostat over a period of 4 hours. AUC: Area Under Curve. The y-axis (in log scale) represents concentration (in nM) of the test compound detected at a specific time-point.

To determine the pharmacokinetic distribution of tosedostat in the body, the test compound was dissolved in 50% saline in DMSO solution and a dosage of 10 mg/Kg was administered to mouse peritoneum. Brain and plasma samples were harvested and analyzed via LC-MS/MS for the presence of tosedostat over a period of 4 hours. These pharmacokinetic experiments showed minimal presence of tosedostat in the brain homogenate samples as compared to the plasma samples (FIG. 16). The absence of tosedostat in brain samples confirmed that the potent analgesic effect observed in systemically administered animal groups stems from its action on the peripheral nervous system.

Opioid Antagonist Naloxone Attenuates the Antinociceptive Effect

Figure 17:
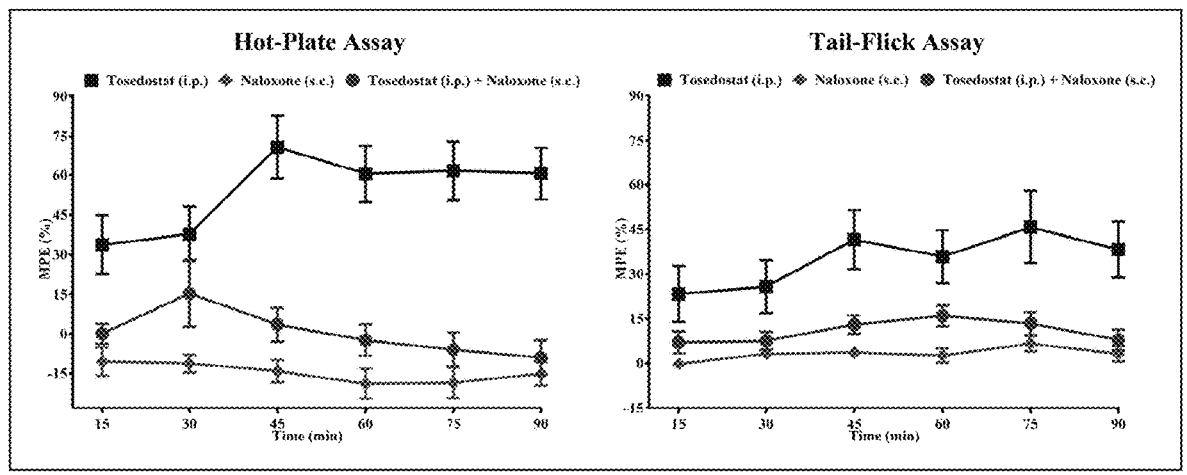
FIG. 17. Effect of co-administration of opioid antagonist naloxone in mouse hot-plate and tail-flick assays. The test compound (■) was dissolved in 50% saline in DMSO solution and delivered intraperitoneally. Naloxone (♦) dissolved in saline, was injected subcutaneously (5 mg/Kg). For the co-administered animal group (●), tosedostat was delivered intraperitoneally followed by subcutaneous administration of naloxone after 5 minutes. The y-axis represents the effect of the dose expressed in percentage of maximum possible effect (% MPE). Error bars represent ±SEM for each time-point with n≥8 animals/time-point. Dosage for i.c.v. injection=100 µg per mouse. Dosage for i.p. delivery=58.1 mg/Kg each mouse. N=8-13 mice (hot-plate assay); N=8-17 mice (tail-flick assay).
Figure 18A:
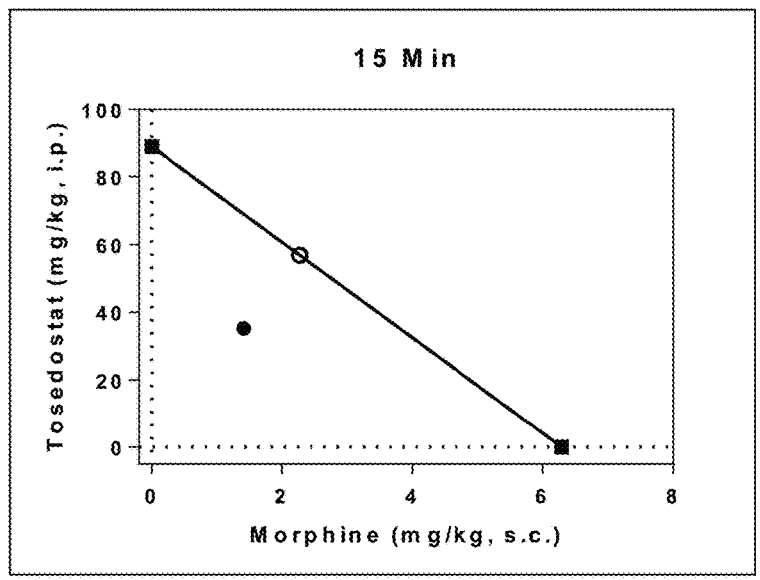
FIGS. 18A-18D. Isobolograms for the combination therapy studies with tosedostat and morphine in tail-flick anti-nociception assay. Tosedostat was administered intraperitoneally. Morphine was delivered subcutaneously. Theoretical additive $ED_{50}$ values (○) for the drug combinations were calculated by utilizing JFlashCalc software package for comparison with experimentally determined $ED_{50}$ values (●) for the combination dosages.
Figure 18B:
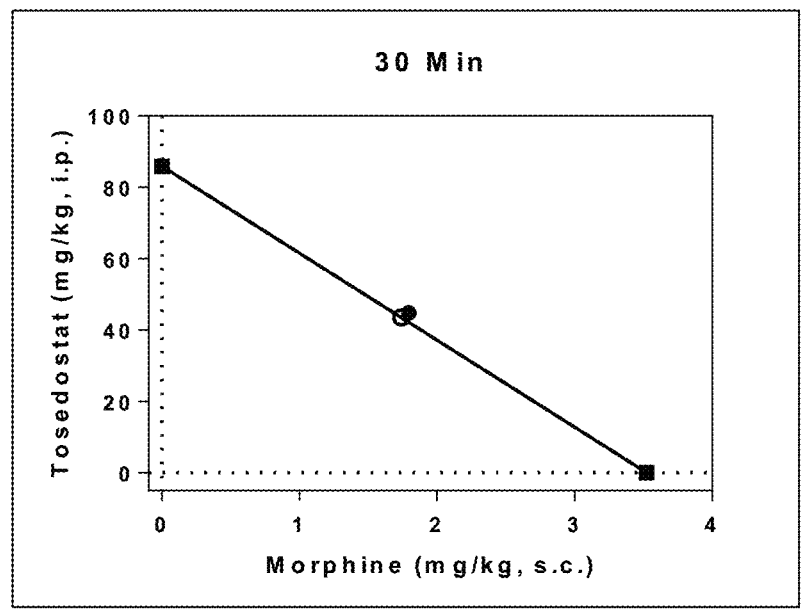
Figure 18C:
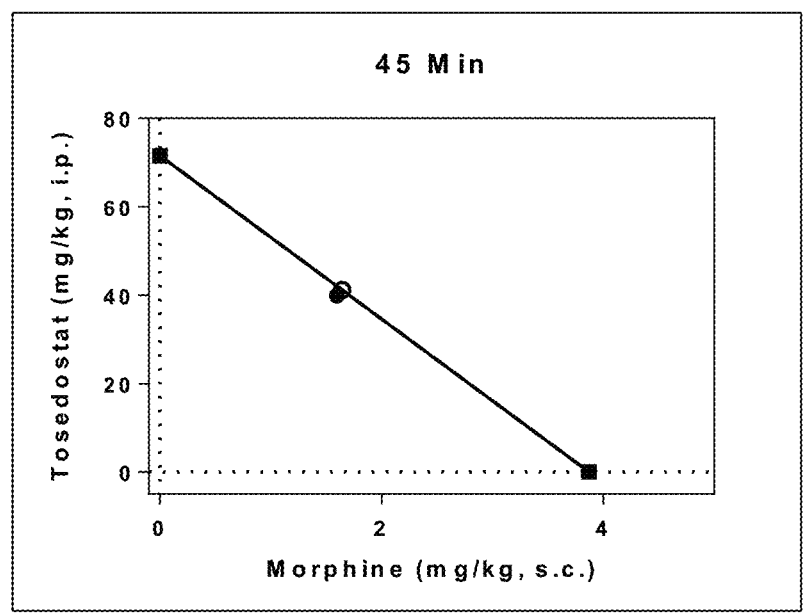
Figure 18D:
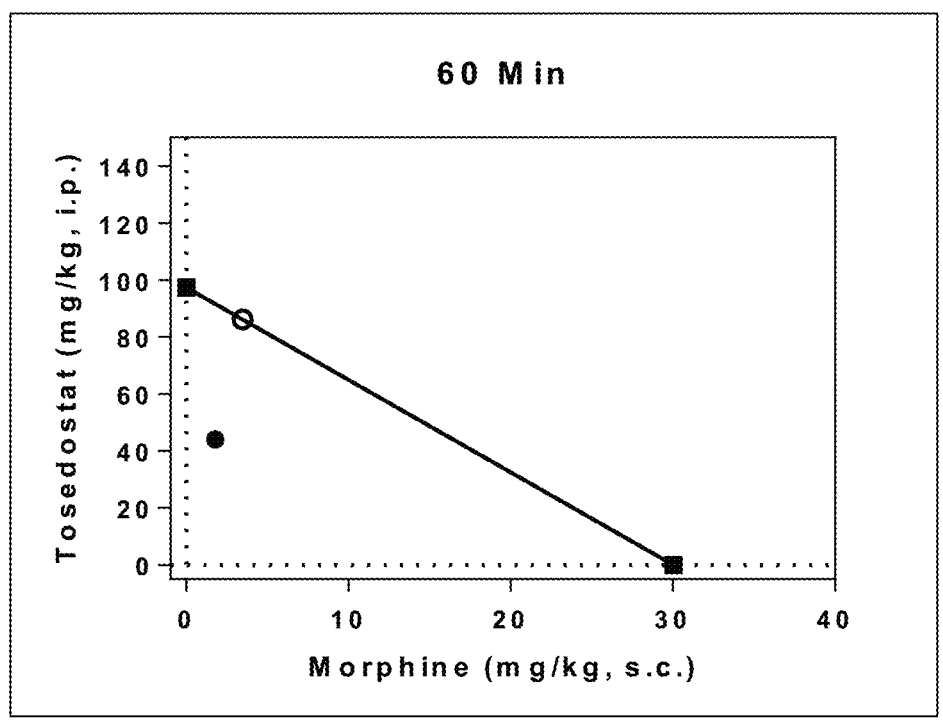

To verify the involvement of opioid receptors in the observed antinociceptive activity, the effect of the opioid receptor antagonist, naloxone on the antinociceptive effect studies was evaluated. Naloxone is a broad-spectrum opioid receptor antagonist. It is known to interact with, mu- ($\mu$-), delta- ($\delta$-), and kappa- ($\kappa$-) opioid receptors, with highest affinity for the $\mu$ receptors. Tosedostat was injected intraperitoneally. Naloxone dissolved in saline was delivered subcutaneously (s.c.) via an injection to the interscapular skin. FIG. 17 shows that while administration of tosedostat triggered a nociceptive response, the naloxone only animal groups had no effect on latency. Subcutaneously administered naloxone partially blocked the analgesic action of tosedostat in both hot-plate and tail-flick assays. Results from this test provide concrete support for the involvement of opioid receptors in the observed analgesic activity of tosedostat (FIG. 17). Similar trends were observed in both the experimental pain models.

Combination Therapy with Morphine

The success of strategic combining of two or more drugs to achieve optimum clinical outcomes has rendered the practice of combination therapy a viable tool in chemical therapeutics. Potentiated efficacy without increasing the adverse effects is the primary goal of this approach. Decreasing toxic side-effects while maintaining efficacy is also a desirable outcome. Additionally, these results usually aid in achieving better patient compliance. The performance of tosedostat in the presence of the well-known potent opioid receptor agonist morphine was also evaluated. Isobolographic analysis was performed to analyze the interactive properties of the two drugs. To determine an equipotent dose ratio, dose-response curves for the analgesic effects for tosedostat and morphine given alone were obtained in tail-flick experiment. $ED_{50}$ value for tosedostat was determined to be from 58.1 mg/Kg to 82 mg/Kg over a period of 60 minutes post injection. For morphine, it was found to be between 2.5 mg/Kg and 3 mg/Kg during the same time period. JFlashCalc software package was utilized to perform the isobolographic analyses (Table 2). The interaction index ($\gamma$) is defined by the equation:

$$\gamma = a/A + b/B$$

where A and B are the doses of drugs A and B alone that gave effect equivalent to 50% MPE ($ED_{50}$) and (a, b) is the combination dose that produced this same level of effect. As shown in FIGS. 18A-18D, the $ED_{50}$ values of the combination (●) at 15 min and 60 min are lower than the theoretical additive $ED_{50}$ values (○), indicating that the interaction is synergistic. The interaction index for the combination at 15 and 60 minutes post-treatment was calculated as 0.6201 and 0.5115, respectively (Table 2; $\gamma<1$ is synergistic). Dose reduction index (DRI) is defined as a measure of the reduction of dosage of a drug in synergistic combination, as compared to each drug alone. At 60 minutes time-point, a DRI index value of 17 to achieve 50% efficacy, indicates towards the potential of a substantial reduction of morphine dosage when combined with tosedostat, as compared to the levels of this often-abused opioid drug required to achieve an equipotent effect when administered solo.

TABLE 2

| Time (min) | Morphine $ED_{50}$ (±SEM) | Tosedostat $ED_{50}$ (±SEM) | Observed Combination $ED_{50}$ (±SEM) | Theoretical Combination $ED_{50}$ (±SEM) | Interaction Index ($\gamma$) | Dose Reduction Index (DRI) | | P-value | Interaction |
|---|---|---|---|---|---|---|---|---|---|
| | | | | | | Morphine | Tosedostat | 0.192* | Additive |
| 15 | 6.29 ± 12.7 | 89.0 ± 109 | 36.7 ± 18.2 | 59.1 ± 63.1 | 0.620 | 4.47 | 2.52 | 0.921 | Additive |
| 30 | 3.52 ± 7.20 | 85.8 ± 132 | 46.6 ± 13.5 | 45.2 ± 57.6 | 1.032 | 1.96 | 1.91 | 0.786 | Additive |
| 45 | 3.87 ± 2.04 | 71.5 ± 47.6 | 41.5 ± 6.04 | 42.8 ± 19.0 | 0.970 | 2.43 | 1.79 | 0.047 | Synergistic |
| 60 | 30.0 ± 204 | 97.3 ± 33.6 | 45.8 ± 9.33 | 89.6 ± 75.1 | 0.511 | 17.0 | 2.21 | 0.192* | Additive |
| 15 | 6.29 ± 12.7 | 89.0 ± 109 | 36.7 ± 18.2 | 59.1 ± 63.1 | 0.620 | 4.47 | 2.52 | 0.921 | Additive |

Molecular Modeling and Docking Studies

To gain a better understanding of the observed bioactivity results, molecular modeling analysis was performed by docking tosedostat in active sites of APN and NEP. X-ray crystallographic structure of human APN in complex with bestatin (PDB code: 4FYR), and NEP in complex with antihypertensive prodrug sacubitrilat (PDB code: 5JMY) were imported into the workspace and refined with the Protein Preparation Wizard implemented in Maestro 11.8.012 of Schrodinger suite 2018.4. The treatment with Protein Preparation Wizard entailed addition of missing hydrogens atoms, removal of water molecules beyond 5 Å from hetero groups, creation of zero-order bonds to metals, followed by the generation of metal binding states. Comprehensive structures were obtained by adding missing side-chains and loops by utilizing Prime. Next, the structures of the proteins were minimized using OPLS3e force field to optimize hydrogen bonding network and converge heavy atoms to an RMSD of 0.3 Å. The OPLS3e force field affords an unprecedented small molecule torsion parameter coverage with improvement in the accuracy of predicted energies. The receptor grid generation tool in Maestro (Schrodinger Inc.) was then used to define active sites around the respective native ligands for both the enzymes. To generate flexible grids, van der Waals radii of non-polar atoms in the receptors were scaled by a factor of 0.8. To make sure that only non-polar atoms are scaled, partial charge cut-off was set to 0.25. The generated receptor grid models were validated by docking the two native ligands from the crystal structures of their respective proteins. Bestatin and sacubitrilat were sketched using Maestro and subjected to LigPrep to generate conformers incorporating metal states in the pH range of 7±3 to be utilized for comparison between the docked and the crystallographic conformations of the ligands. All the dockings were performed using Glide in Extra Precision (XP) mode with $Zn^{2+}$ metal co-factor as a constraint. The ligands were sampled as flexible entities for docking. Strain correction terms were applied and finally, post-docking minimization was performed on the generated poses.

Figure 19A:
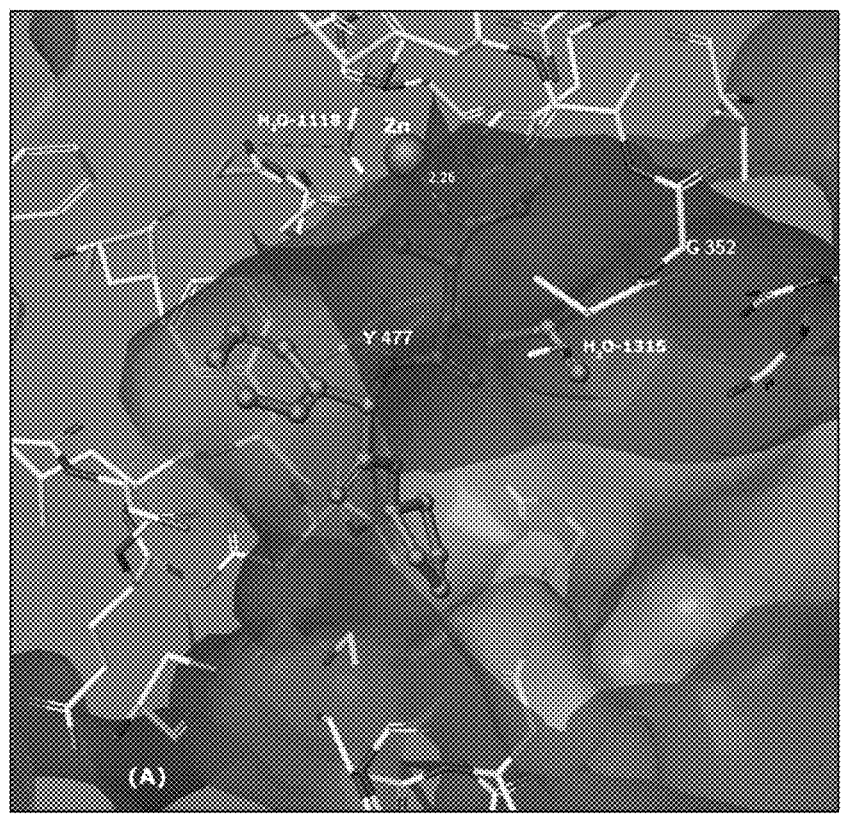
FIGS. 19A-19B. Tosedostat (center) docked in the binding site of (FIG. 19A) Aminopeptidase N—PDB code 4FYR (FIG. 19B) Neprilysin—PDB code 5JMY $Zn^{2+}$ cation is depicted as a sphere. The proteins are labeled in accordance with the reported crystal structures from the respective PDB files of the enzymes. Dashed lines represent Ligand-Receptor interactions: Hydrogens from ligands and receptors are removed for clarity.
Figure 19B:
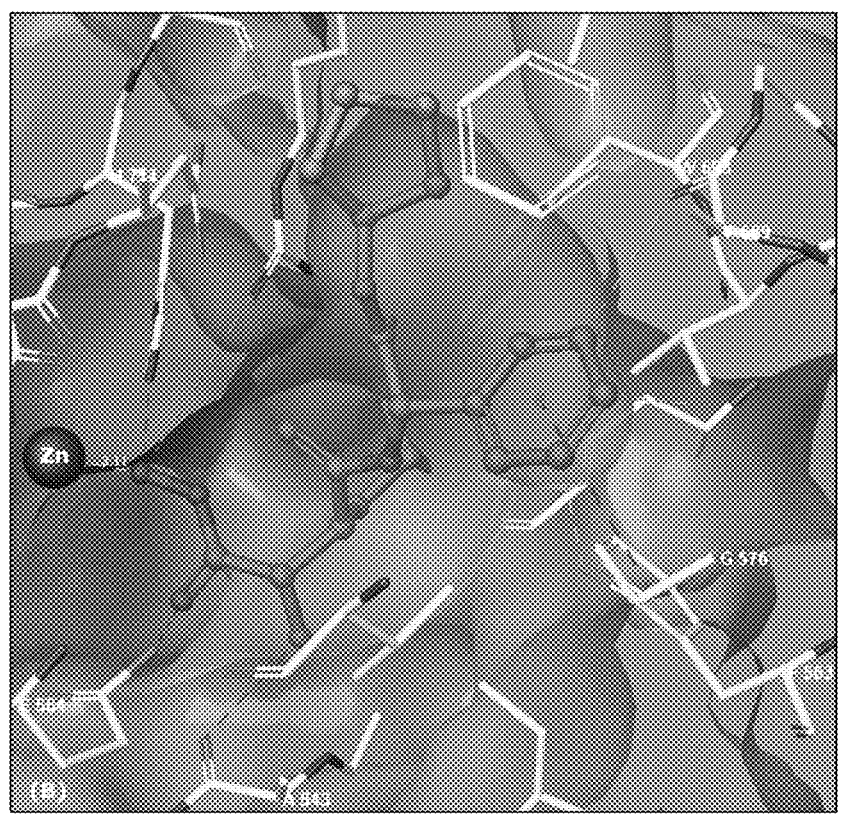

Validation of the two models was followed by docking of tosedostat and batimastat in the binding pockets of the two enzymes. First, tosedostat and batimastat were sketched using the 2-D sketcher tool and converted to three-dimensional structures in Maestro. Minimization utilizing OPLS3e force field was followed by generating various conformers of the two compounds by LigPrep. Ligand structures sampled as flexible entities were then docked in the receptor grids for both APN and NEP. Highest ranked poses for tosedostat docked in the binding pockets of APN and NEP are presented in FIGS. 19A-19B.

The calculated docking scores for these studies represent an estimation of binding energies for the ligand-receptor complexes. A binding energy score of −6.419 kcal/mol was obtained for the docking of tosedostat in the active site of APN indicating strong interactions between the ligand and the metalloenzyme. The proximity of carbonyl oxygen of the hydroxamic acid functional group to the zinc cation (2.26 Å) provides a strong incentive for metal ligation. The phenyl group on the molecule extends into the hydrophobic pocket potentiating the ligand-receptor interaction. Tyrosyl residue Tyr477 seems to play a significant role in this binding by making itself available for hydrogen bonding via the para-hydroxyl moiety, thus resulting in a strong binding. Additional stability to this complex is afforded by the formation of hydrogen bonds with multiple solvent molecules ($H_2O$-1118, and $H_2O$-1315). Similar to tosedostat, the presence of hydroxamic acid moiety in batimastat also assisted in its tight binding in the active site of APN. Residues His388, Phe472, and Tyr477 confer stability to the complex via aromatic-H bond interactions. Phe472 is also in a favorable position to contribute by hydrogen bond formation. The stabilization afforded by these ligand-receptor interactions for batimastat in the binding pocket of APN translate to a docking score of −6.856 kcal/mol.

In the case of NEP, tosedostat displayed stronger binding furnishing a calculated binding energy of −12.636 kcal/mol. Several key interactions reinforcing tighter binding interactions were observed. Namely, residues Ala543, Glu584, Trp693, His711, and Arg717 display proclivity to participate in hydrogen bonding with the ligand. Additional stability could be afforded via aromatic-H bond interactions of the ligand with Gly576, Phe689, and Trp693, along with π-π stacking with Phe563. For batimastat docked in NEP, hydrogen bonding with His711 and Arg717, along with aromatic-H bonding with His587 were found to stabilize the complex. Π-π stacking interactions with Phe544 and Trp693 contributed towards giving it a strong docking score of −10.223. Interestingly, both oxygen atoms of the hydroxamic acid functional group were found to be equidistant from the zinc cation (2.33 Å). The in silico calculations of docking tosedostat and batimastat in NEP followed the reactivity trend observed in the biochemical assays. Experimentally determined $IC_{50}$ value of 0.89 µM for tosedostat and 4.48 µM for batimastat corresponded to a better docking score for tosedostat in NEP as compared to the docking score of batimastat in APN. Similarly, with $IC_{50}$ values of 0.93 µM for tosedostat, and 0.21 µM for batimastat recorded in the experimental assays against APN (Table 1), the docking scores obtained for APN also provide undeniable support for the observed reactivity trends noted above.

CONCLUSIONS

Tosedostat is an inhibitor of aminopeptidases currently in phase II clinical trial for treatment of blood related cancers. It has now been shown to possess analgesic properties. This is a significant alternate use for this compound. In vivo antinociceptive studies demonstrated that the observed analgesic effect is largely restricted to the peripheral nervous system. Analgesic effect produced by impeding the breakdown of endogenous neuropeptides avoids overstimulation of pain related receptors. This results in no development of dependency, addiction or increased tolerance to analgesic effects. It has been determined that tosedostat concomitantly inhibits two endopeptidases implicated in rapid inactivation of endogenous neuropeptides. Furthermore, tosedostat is already undergoing human clinical trials for anticancer activity. Its toxicity and side effects are currently being evaluated and studied extensively in clinical settings making this an attractive tool in combating the opioid epidemic.

EXPERIMENTAL SECTION

General. General Procedures

Chemicals and Reagents. Tosedostat was purchased from eNovation Chemicals, LLC. Aminopeptidase N was purchased from R&D Systems. Neprilysin was purchased from Enzo Life Sciences. Thiorphan was purchased from Cayman chemicals. Bestatin was purchased from Alfa Aesar. All other chemicals and reagents used in this study were purchased from Sigma-Aldrich, unless otherwise stated.

Animals

Drug-naive, adult male CF-1 mice (275-300 g, Envigo, East Millstone, N.J.) of ages between 5 and 7 weeks were allowed to acclimate to the facility for several days. For all experiments, animals were housed three per cage, in a controlled environment (22° C., RH 50-60%, light from 07:00-19:00 h). Food and water were made available ad libitum. All experimental procedures and animal handling were executed in accordance with the national ethics guidelines, approved, and complied with all protocol requirements at the University of Minnesota, Minneapolis, Minn. (IACUC).

Preparation of Drugs and Dosages

All tested drug compounds and their solutions were stocked at −20° C. until ready to be used. Prior to drug administration, weighed, and separated into different treatment groups. Food was kept out of the cages until after the final drug injection.

Anti-Aminopeptidase Enzyme Studies for APN

Single concentration studies at 10 µM: Aminopeptidase N assays were performed as described previously. Aminopeptidase N was purchased from R&D Systems. Amino-4-methylcoumarin (Ala-AMC) was purchased from Bachem. Briefly, 0.1 µg/µL APN was incubated with 1 µL of 1 mM inhibitor in 50 mM Tris buffer, pH 7.5, in 100 µL volume in a black 384-well plate in duplicate. The reaction was started with the addition of Ala-AMC substrate at a final concentration of 100 µM. The cleavage accumulation AMC was measured by exciting at 380 nm and reading the fluorescence at 460 nm on a Molecular Devices SpectraMax i3 plate reader for 20 min at room temperature. Percent inhibition is calculated in GraphPad Prism software using slopes in the linear range for each inhibitor at 10 µM.

Dose-Response Studies for APN: Aminopeptidase N enzyme assays were performed as described previously.[26] Briefly, 0.1 µg/µL APN was incubated with 1 µL inhibitor in 50 mM Tris buffer, pH 7.5, in 50 µL volume in a black 384-well plate in duplicate. Compounds were tested at 3× dilutions from 100 µM final concentration. The reaction was started with the addition of Ala-AMC substrate at a final concentration of 100 µM. The accumulation of AMC was measured by exciting at 380 nm and reading the fluorescence at 460 nm on a Molecular Devices SpectraMax i3 plate reader for 30 min at room temperature. Steady state velocities were used to determine $IC_{50}$ values by fitting the velocities vs. inhibitor concentration to the sigmoidal concentration-response curve (variable slope) using GraphPad Prism.

Anti-Aminopeptidase Enzyme Studies for NEP

Single concentration studies at 10 µM: Neprilysin inhibition assays were performed as described previously. The substrate Mca-RPPGFSAFK(Dpn) and endopeptidase NEP were purchased from Enzo Life Sciences. Briefly, 0.5 nM NEP was incubated with 10 µM of inhibitor (thiorphan added as a control) in 50 mM HEPES pH 6.5 in 50 µL total volume in a black 384-well plate. Plate was mixed with a plate shaker at 1500 rpm for 30 seconds. The reaction was started with the addition of 6 µM of the FRET substrate and mixed for another 30 seconds at 1500 rpm. Mca fluorescence is quenched by Dpn until cleavage at Phe by NEP. The accumulation of the Mca was measured by exciting at 320 nm and reading the fluorescence at 405 nm on a Molecular Devices M5e plate reader for 40 minutes at room temperature. Percent inhibition is calculated in GraphPad Prism software using slopes in the linear range for each inhibitor at 10 µM.

Dose-Response Studies for NEP: Neprilysin inhibition assays were performed as described previously. The substrate Mca-RPPGFSAFK(Dpn) and endopeptidase NEP were purchased from Enzo Life Sciences. Briefly, 0.5 nM NEP was incubated with 0.5 µL inhibitor. Compounds were tested at 3× dilutions from 100 µM final concentration in 50 mM HEPES pH 6.5 in 50 µL total volume in a black 384-well plate. Plate was mixed with a plate shaker at 1500 rpm for 30 seconds. The reaction was started with the addition of 6 µM of the FRET substrate and mixed for another 30 seconds at 1500 rpm. Mca fluorescence is quenched by Dpn until cleavage at Phe by NEP. The accumulation of the Mca was measured by exciting at 320 nm and reading the fluorescence at 405 nm on a Molecular Devices M5e plate reader for 40 minutes at room temperature. Steady state velocities were used to determine $IC_{50}$ values by fitting the velocities vs. inhibitor concentration to the sigmoidal concentration-response curve (variable slope) using GraphPad Prism.

Hot-Plate Method

Analgesic potencies of control and test compounds were determined in male CF1 mice using the hot-plate model. The hot-plate was the top surface of an enclosed cylindrical glass bath through which thermostatically controlled hot water was circulated. Under the conditions used, the temperature of the surface of the cylinder was maintained at 55° C. Baseline reaction time control values were determined for each test animal at 15 minute intervals half an hour before administering the test compounds by placing the animal on the hot surface of the instrument and recording the reaction time when it either exhibited hind-paw shake/lift, hind-paw lick, or jumped off of the platform. Test compounds were administered via intraperitoneal (i.p.) or intracerebroventricular (i.c.v.) routes. Tosedostat was dissolved in 50% DMSO and saline solution. At various time points post-injection (15, 30, 45, 60, 75, and 90 min), mice were placed on the hot surface and the time recorded when mice either exhibited hind-paw shake/lift, hind-paw lick, or jumped off of the platform as their reaction times. Animals with a mean reaction time greater than 13 seconds were excluded as non-responders. For animals which did not leave the hot surface, a cut-off time of 60 seconds was used to avoid injury to their tissue. The observed analgesic effects are presented as the percentage maximum possible effect (% MPE) calculated by % MPE=(Test−Baseline)/(Cutoff−Baseline)× 100, where Test is the observed latency to respond after the treatment, Baseline is the latency to respond prior to the treatment, and Cutoff is the time at which the test is ended in the absence of a response from the animal −60 seconds for these experiments.

Tail-Flick Assay

Columbus Instruments tail-flick analgesiometer was employed for this experiment. Male CF-1 mice were gently restrained in a cloth; the tail-flick beam was centered on the dorsal surface of the tail (about 15 mm from the end of the tail). The heat source was activated, and the latency for withdrawal of the tail recorded. The intensity of the tail-flick beam was adjusted so that the average withdrawal time of the baseline measurement was 2 to 4 sec. For each animal, a baseline response latency was determined in two consecutive responses measured at 5 min intervals. Test compounds were administered systemically (i.p.) or centrally (i.c.v.) to the mice. The tail-flick response of the animals was tested at 15, 30, 45, 60, 75, and 90 minutes after drug administration. To protect against tissue injury, the test was terminated after 10 seconds if the animal did not withdraw its tail.

Antinociceptive Behavioral Test for Persistent Pain: Acetic Acid Writhing Test

The mice were given vehicle or test compounds 15 min before acetic acid administration. Subsequently, all the groups of mice were injected with 1% (10 mL/kg) acetic acid solution intraperitoneally to induce writhing. The animals display characteristic movements such as extension of hind limb, abdominal constriction, and trunk twisting movement called writhing. The numbers of writhing episodes in 30 min period beginning at the time of the acetic acid administration were counted. Tosedostat was dissolved in 50% saline in DMSO solution. APAP was dissolved in saline. Both test compounds were delivered intraperitoneally to the test animals.

Antinociceptive Behavioral Test for Persistent Pain: Formalin Test

Mice were injected with 20 µl of 2% buffered formalin solution into the intraplantar region of hind paw of mice and the total time spent in licking and biting of the formalin-treated paw by the animals over the course of 30 min (phase I, acute pain behavior, 0-5 min; phase II, chronic pain behavior, 15-30 min) was recorded. Test compounds were injected 15 min prior to formalin administration. The pain response time (licking time) was recorded for every 5-min period during the 30-min recording for each mouse. The test compounds were dissolved in 50% saline in DMSO solution and delivered systemically Determination of Distribution of Tosedostat in Brain and Plasma Dosing and sample collection: A 2 mg/ml solution of tosedostat in 50% DMSO in saline was prepared and injected into the mouse peritoneum at dosage of 10 mg/Kg of body weight of the animal. The subjects were intraperitoneally injected with ketamine-xylazine cocktail (100 mg/kg ketamine+10 mg/kg xylazine) 2 minutes prior to the time-point being analyzed. Specifically, samples were collected at 0.25, 0.5, 1, 2, and 4 hours after the drug administration. Once the animals failed to respond to stimuli towards their paws, blood samples were collected via cardiac puncture bleeding into EDTA-K2 coated tubes. Samples were immediately centrifuged at 3000×rpm for 10 minutes at 4° C. and the separated top plasma layer was transferred into a new tube. Blood samples stored at −80° C. until LC-MS/MS analysis. For brain samples, brain tissue was extracted from the animal and washed with copious volumes of ice-cold D-PBS for removal of blood from the sample. and Collect brain and wash the brain with ice-cold DPBS properly to remove blood. The sample was then gently wiped with absorbent paper, weighed, and transferred into a 15 mL tube. The brain samples were homogenized by adding 1:5 (w/v) of ice-cold D-PBS into the tube and using mechanical homogenizer on them. Homogenized brain samples were also stored at −80° C.

LC-MS/MS analysis: Frozen plasma and brain homogenate samples were thawed and rapidly quenched as detailed here. For plasma samples, 30 μL of DMSO and 60 μL of acetonitrile containing 0.1% formic acid were added to 30 μL of each unknown thawed plasma sample. For brain homogenate samples, 10 μL of DMSO and 60 μL of acetonitrile containing 0.1% formic acid were added to 30 μL of each unknown sample. The samples were then vortexed and centrifuged at 15,000 rpm for 5 min at 4° C. The supernatants were injected in an Agilent 1260 Infinity LC instrument equipped with a Phenomenex Kinetex C18 column (50×2.1 mm, 2.6 μm). For mobile phase, a gradient of 10% to 90% with deionized water (+0.1% formic acid) and acetonitrile (+0.1% formic acid) was utilized. A flow rate of 0.5 mL/min was maintained for the run of the samples. For MS/MS analysis, AB Sciex QTRAP® 5500 instrument with Turbo VTM ESI(+ve) ion source was employed. The concentration-time curves for tosedostat in both plasma and brain were analyzed using Phoenix WinNonlin 7.0 using non-compartmental model. The obtained AUCs (area under curve) were used to calculate the brain to plasma ratio ($AUC_{brain}/AUC_{plasma}$).

Effect of Opioid Antagonist Naloxone

Tosedostat (58.1 mg/Kg) was dissolved in 50% saline in DMSO solution and administered intraperitoneally. 5 mg/Kg naloxone dissolved in saline was administered subcutaneously (s.c.) via an injection to the interscapular skin. Analgesic efficacy for various time-points was determined in hot-plate and tail-flick assays as detailed above.

Combination Therapy with Morphine

To perform isobolographic analysis, dose-response curves for both the agonists were obtained. Tosedostat dissolved in 50% saline/DMSO solution was delivered intraperitoneally to mice at the dosages of 30 mg/Kg, 58.3 mg/Kg, 75 mg/Kg, and 100 mg/Kg. Morphine was dissolved in saline and administered subcutaneously at the dosages of 1, 1.5, 2, and 2.5 mg/Kg. Individual analgesic potency for tosedostat and morphine were determined for 15, 30, 45, and 60 minute time-points in tail-flick assay. The $ED_{50}$ values were calculated for both the compounds and an equi-effective dose ratio of 1:25 (morphine: tosedostat) was determined. This ratio was maintained for the combined dosages. Animal groups were administered the following combined dosages: tosedostat (62.5 mg/Kg)+morphine (2.5 mg/Kg); tosedostat (50 mg/Kg)+morphine (2 mg/Kg); tosedostat (37.5 mg/Kg)+morphine (1.5 mg/Kg); and tosedostat (25 mg/Kg)+morphine (1 mg/Kg). Analgesic potency of the combined dosages was determined in tail-flick assay and experimentally derived $ED_{50}$ values were obtained for these dosages at various time-points. Based on dose-response curve of each agonists administered separately, a theoretical $ED_{50}$ value for the combination dosages was calculated for each time-point by utilizing the JFlashCalc software package. With dosage concentration of tosedostat as y-axis and dosage concentration of morphine as x-axis, isobolograms were then constructed by plotting the experimentally determined $ED_{50}$ values for individual agonists, theoretically determined $ED_{50}$ value for the combined dosages, and experimentally determined $ED_{50}$ values for the combined dosages. Interaction index values for each time-point were calculated using the JFlashCalc software package.

Molecular Modeling and Docking Studies

Molecular modeling was performed using the Schrodinger Small-Molecule Drug Discovery Suite 2018-4. The crystal structures of neprilysin in complex with sacubitrilat (PDB code 5JMY), and human aminopeptidase N in complex with bestatin (PDB code 4FYR) were used as starting points. This model was subjected to Protein Preparation Wizard implemented in the Maestro suite of Schrodinger 2018-4. The proteins were prepared by adding missing hydrogen atoms in the structure. Next, removal of water molecules beyond 5 Å from hetero groups was followed by creation of zero-order bonds to metals. Metal binding states were then generated. Comprehensive structures were obtained by adding missing side-chains and loops by utilizing Prime. Additional refinement entailed the optimization of hydrogen bonding network by using PROPKA. Next, the structure of the protein was minimized using OPLS3e force field by converging heavy atoms to RMSD of 0.3 Å. The active site in the refined protein was annotated by using the receptor grid generation tool in Maestro. The grid was set to cover all the residues within 12 Å$^3$ box centered on the respective native ligands, bestatin for APN and sacubitrilat for NEP. $Zn^{2+}$ metal cofactor was used as a constraint during docking. To generate flexible grids, van der Waals radii of non-polar atoms in the receptor were scaled by a factor of 0.8. To make sure that only non-polar atoms are scaled, partial charge cut-off was set to 0.25. The generated receptor grid model was validated by docking the two native ligands from the crystal structures of the two proteins. Bestatin, sacubitrilat, tosedostat, and batimastat were sketched using Maestro and subjected to LigPrep to generate conformers incorporating metal states in the pH range of 7±3 to be utilized for the docking process. All the dockings were performed using Glide in Extra Precision (XP) mode with $Zn^{2+}$ metal co-factor as constraint. To soften the potential of non-polar parts of the ligands, the van der Waals radii of ligand atoms were scaled by a factor of 0.60 with a partial charge cut-off of 0.15. All the ligands were sampled as flexible entities for docking. Strain correction terms were applied and finally, post-docking minimization was performed on the generated poses.

Statistics and Graphics

All data presented are shown as mean±SEM, unless otherwise noted. Significance was designated at $p<0.05$. Graphical depictions and statistical analyses were carried out using GraphPad Prism 6 or 7 (GraphPad Software, Inc., La Jolla, Calif.). Microsoft Excel 2016 was used to calculate correlation values.

The invention has been described with reference to various specific and preferred embodiments and techniques. However, it should be understood that many variations and modifications may be made while remaining within the spirit and scope of the invention.

All publications, patents, and patent documents (including International Patent Application Publication Number WO 1999/046241 and U.S. Pat. Nos. 6,169,075 and 6,462,023) are incorporated by reference herein, as though individually incorporated by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for treating pain in an animal comprising administering to the animal an effective pain-relieving amount of a compound of formula (I):

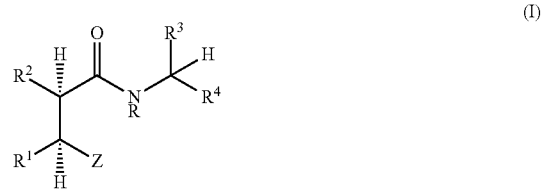

wherein:
R is hydrogen or $(C_1-C_6)$alkyl;
$R^1$ is hydrogen, $(C_1-C_6)$alkyl, $(C_2-C_6)$alkenyl, phenyl, phenyl$(C_1-C_6)$alkyl, phenyl$(C_2-C_6)$alkenyl, heterocyclyl, heterocyclyl$(C_1-C_6)$alkyl, hydroxyl, $(C_1-C_6)$alkoxy, —$NH_2$, —C(=O)$NH_2$, $(C_1-C_6)$alkylamino, di$(C_1-C_6)$alkylamino, mercapto, $(C_1-C_6)$alkylthio, (heteroaryl)thio$(C_1-C_6)$alkyl, amino$(C_1-C_6)$alkyl, $(C_1-C_6)$akylamino$(C_1-C_6)$alkyl, di$(C_1-C_6)$alkylamino$(C_1-C_6)$alkyl, hydroxy$(C_1-C_6)$alkyl, mercapto$(C_1-C_6)$alkyl, carboxy$(C_1-C_6)$alkyl, lower alkyl substituted by carbamoyl, mono$((C_1-C_6)$alkyl)carbamoyl, di$((C_1-C_6)$alkyl)carbamoyl, di$((C_1-C_6)$alkyl)amino, or carboxy-lower alkanoylamino, $R^a$, or a group $BSO_nA$-; or $R^1$ and $R^2$ taken together with the atoms to which they are attached form a 4-, 5-, 6-, or 7-membered saturated or partially unsaturated carbocycle or a 4-, 5-, 6-, or 7-membered saturated or partially unsaturated heterocycle that comprises carbon and one or two heteroatoms selected from O, S, and $NR^d$, wherein $R^d$ is H or $(C_1-C_4)$alkyl;
n is 0, 1 or 2;
B is hydrogen, $(C_1-C_6)$alkyl, phenyl, heterocyclyl, $(C_1-C_6)$alkanoyl, or phenyl-C(=O)—;
A is $(C_1-C_6)$alkylene,
$R^a$ is a cycloalkyl, a cycloalkenyl, or a non-aromatic heterocyclic ring containing up to 3 heteroatoms, any of which may be (i) substituted by one or more substituents selected from $(C_1-C_6)$alkyl, $(C_2-C_6)$alkenyl, halo, cyano, carboxy, —$CO_2R^b$, —$CONH_2$, —$CONHR^b$, —$CON(R^b)_2$, —OH, —$OR^b$, oxo, —SH, —$SR^b$, —$NHCOR^b$, and $NHCO_2R^b$; or (ii) fused to a cycloalkyl or heterocyclic ring;
$R^b$ is $(C_1-C_6)$alkyl or benzyl;
$R^2$ is $(C_1-C_{12})$alkyl, $(C_2-C_{12})$alkenyl, $(C_2-C_{12})$alkynyl, phenyl$(C_1-C_6)$alkyl-, heteroaryl$(C_1-C_6)$alkyl-, phenyl$(C_2-C_6)$alkenyl-, heteroaryl$(C_2-C_6)$alkenyl-, phenyl$(C_2-C_6)$alkynyl-, heteroaryl$(C_2-C_6)$alkynyl-, cycloalkyl$(C_1-C_6)$alkyl-, cycloalkyl$(C_2-C_6)$alkenyl-, cycloalkyl$(C_2-C_6)$alkynyl-, cycloalkenyl$(C_1-C_6)$alkyl-, cycloalkenyl$(C_2-C_6)$alkenyl-, cycloalkenyl$(C_2-C_6)$alkynyl-, phenyl$(C_1-C_6)$alkyl-O$(C_1-C_6)$alkyl-, or heteroaryl$(C_1-C_6)$alkyl-O—$(C_1-C_6)$alkyl- any one of which may be optionally substituted by $(C_1-C_6)$alkyl, $(C_1-C_6)$alkoxy, halo, cyano, phenyl, or phenyl that is optionally substituted by $(C_1-C_6)$alkyl, $(C_1-C_6)$alkoxy, halo, or cyano;
$R^3$ is the side chain of a natural or a non-natural α-amino acid;
$R^4$ is an ester group, a thioester group, aminocarbonyl, $(C_1-C_6)$alkylaminocarbonyl, or di$(C_1-C_6)$alkylaminocarbonyl; and
Z is selected from —CONHOH, —$COOR^c$, —CONHOR$^c$, —$CONR^cOH$, —$CONHS(O)_2R^c$, —$CONH_2$, —$CONHR^c$, and —$P(O)(OH)_2$, wherein $R^c$ is $(C_1-C_4)$alkyl, aryl$(C_1-C_4)$alkyl-, or heteroaryl$(C_1-C_4)$alkyl-;

or a pharmaceutically acceptable salt thereof;
wherein any phenyl or heterocyclyl of $R^1$ is optionally substituted with up to four substituents, each of which independently may be selected from $(C_1-C_6)$alkyl, $(C_1-C_6)$alkoxy, hydroxy, mercapto, $(C_1-C_6)$alkylthio, amino, halo, nitro, trifluoromethyl, —COOH, —CONH$_2$, cyano, —COOR$^A$, —COONHR$^A$ or —COONR$^A$R$^A$ wherein R$^A$ is a $(C_1-C_6)$alkyl group or the residue of a natural alpha-amino acid.

2. The method of claim 1, wherein:
R is hydrogen or $(C_1-C_6)$alkyl;
$R^1$ is hydrogen, $(C_1-C_6)$alkyl, $(C_2-C_6)$alkenyl, phenyl, phenyl$(C_1-C_6)$alkyl, phenyl$(C_2-C_6)$alkenyl, heterocyclyl, heterocyclyl$(C_1-C_6)$alkyl, hydroxyl, $(C_1-C_6)$alkoxy, —NH$_2$, —C(=O)NH$_2$, $(C_1-C_6)$alkylamino, di$(C_1-C_6)$alkylamino, mercapto, $(C_1-C_6)$alkylthio, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl, mercapto$(C_1-C_6)$alkyl, or carboxy$(C_1-C_6)$alkyl, lower alkyl substituted by carbamoyl, mono$((C_1-C_6)$alkyl)carbamoyl, di$((C_1-C_6)$alkyl)carbamoyl, di$((C_1-C_6)$alkyl)amino, or carboxy-lower alkanoylamino, R$^a$, or a group BSO$_n$A-; or $R^1$ and $R^2$ taken together with the atoms to which they are attached form a 4-, 5-, 6-, or 7-membered saturated or partially unsaturated carbocycle or a 4-, 5-, 6-, or 7-membered saturated or partially unsaturated heterocycle that comprises carbon and one or two heteroatoms selected from O, S, and NR$^d$, wherein R$^d$ is H or $(C_1-C_4)$alkyl;
n is 0, 1 or 2;
B is hydrogen, $(C_1-C_6)$alkyl, phenyl, heterocyclyl, $(C_1-C_6)$alkanoyl, or phenyl-C(=O)—;
A is $(C_1-C_6)$alkylene,
R$^a$ is a cycloalkyl, a cycloalkenyl, or a non-aromatic heterocyclic ring containing up to 3 heteroatoms, any of which may be (i) substituted by one or more substituents selected from $(C_1-C_6)$alkyl, $(C_2-C_6)$alkenyl, halo, cyano, carboxy, —CO$_2$R$^b$, —CONH$_2$, —CONHR$^b$, —CON(R$^b$)$_2$, —OH, —OR$^b$, oxo, —SH, —SR$^b$, —NHCOR$^b$, and NHCO$_2$R$^b$; or (ii) fused to a cycloalkyl or heterocyclic ring;
R$^b$ is $(C_1-C_6)$alkyl or benzyl;
$R^2$ is $(C_1-C_{12})$alkyl, $(C_2-C_{12})$alkenyl, $(C_2-C_{12})$alkynyl, phenyl$(C_1-C_6)$alkyl-, heteroaryl$(C_1-C_6)$alkyl-, phenyl$(C_2-C_6)$alkenyl-, heteroaryl$(C_2-C_6)$alkenyl-, phenyl$(C_2-C_6)$alkynyl-, heteroaryl$(C_2-C_6)$alkynyl-, cycloalkyl$(C_1-C_6)$alkyl-, cycloalkyl$(C_2-C_6)$alkenyl-, cycloalkyl$(C_2-C_6)$alkynyl-, cycloalkenyl$(C_1-C_6)$alkyl-, cycloalkenyl$(C_2-C_6)$alkenyl-, cycloalkenyl$(C_2-C_6)$alkynyl-, phenyl$(C_1-C_6)$alkyl-O$(C_1-C_6)$alkyl-, or heteroaryl$(C_1-C_6)$alkyl-O—$(C_1-C_6)$alkyl- any one of which may be optionally substituted by $(C_1-C_6)$alkyl, $(C_1-C_6)$alkoxy, halo, cyano, phenyl, or phenyl that is optionally substituted by $(C_1-C_6)$alkyl, $(C_1-C_6)$alkoxy, halo, or cyano;
$R^3$ is the side chain of a natural or a non-natural α-amino acid;
$R^4$ is an ester or thioester group; and
Z is selected from —CONHOH, —COOR$^c$, —CONHOR$^c$, —CONR$^c$OH, —CONHS(O)$_2$R$^c$, —CONH$_2$, —CONHR$^c$, and —P(O)(OH)$_2$, wherein R$^c$ is $(C_1-C_4)$alkyl, aryl$(C_1-C_4)$alkyl-, or heteroaryl$(C_1-C_4)$alkyl-;
or a pharmaceutically acceptable salt thereof;
wherein any phenyl or heterocyclyl of $R^1$ is optionally substituted with up to four substituents, each of which independently may be selected from $(C_1-C_6)$alkyl, $(C_1-C_6)$alkoxy, hydroxy, mercapto, $(C_1-C_6)$alkylthio, amino, halo, nitro, trifluoromethyl, —COOH, —CONH$_2$, cyano, —COOR$^A$, —COONHR$^A$ or —COONR$^A$R$^A$ wherein R$^A$ is a $(C_1-C_6)$alkyl group or the residue of a natural alpha-amino acid.

3. The method of claim 1, wherein $R^1$ is hydroxyl.
4. The method of claim 1, wherein $R^2$ is $(C_1-C_{12})$alkyl.
5. The method of claim 1, wherein $R^3$ is phenyl.
6. The method of claim 1, wherein $R^3$ is 2-methylpropyl.
7. The method of claim 1, wherein $R^4$ is cycloalkyl-O—C(=O)—.
8. The method of claim 1, wherein $R^4$ is cyclopentoxycarbonyl.
9. A method for treating pain in an animal comprising administering to the animal an effective pain-relieving amount of tosedostat:

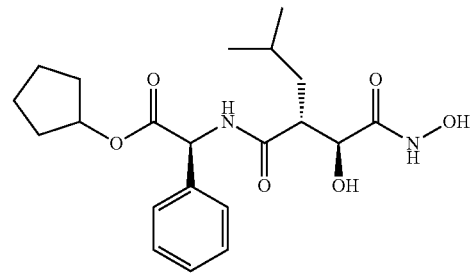 [SMILES: CC(C)C[C@@H](C(=O)N[C@H](C(=O)OC1CCCC1)c1ccccc1)[C@H](O)C(=O)NO]

or a pharmaceutically acceptable salt thereof.

10. The method of claim 1, further comprising administering another analgesic compound to the animal.
11. The method of claim 10 wherein the other analgesic compound is an opioid.
12. The method of claim 1, further comprising administering a therapeutic agent to the animal.
13. The method of claim 12 wherein the therapeutic agent is a non-steroidal anti-inflammatory.
14. The method of claim 1 wherein the compound of formula (I) or the pharmaceutically acceptable salt thereof is administered by injection.
15. The method of claim 1 wherein the compound of formula (I) or the pharmaceutically acceptable salt thereof is administered by intraperitoneal injection.
16. The method of claim 14, wherein the compound of formula (I) or the pharmaceutically acceptable salt thereof is tosedostat or a pharmaceutically acceptable salt thereof.
17. The method of claim 15, wherein the compound of formula (I) or the pharmaceutically acceptable salt thereof is tosedostat or a pharmaceutically acceptable salt thereof.
18. The method of claim 11 wherein the compound of formula (I) or a pharmaceutically acceptable salt thereof is tosedostat or a pharmaceutically acceptable salt thereof.
19. The method of claim 12 wherein the compound of formula (I) or a pharmaceutically acceptable salt thereof is tosedostat or a pharmaceutically acceptable salt thereof.
20. The method of claim 1 wherein:
$R^2$ is $(C_1-C_{12})$alkyl;
$R^3$ is phenyl or 2-methylpropyl; and
$R^4$ is cycloalkyl-O—C(=O)—.
21. The method of claim 1 wherein:
$R^1$ is hydroxyl;
$R^2$ is $(C_1-C_{12})$alkyl;
$R^3$ is phenyl or 2-methylpropyl; and
$R^4$ is cycloalkyl-O—C(=O)—.

22. The method of claim 1 wherein:
$R^2$ is $(C_1$-$C_{12})$alkyl;
$R^3$ is phenyl or 2-methylpropyl; and
$R^4$ is cyclopentoxycarbonyl.

23. The method of claim 1 wherein:
$R^1$ is hydroxyl;
$R^2$ is $(C_1$-$C_{12})$alkyl;
$R^3$ is phenyl or 2-methylpropyl; and
$R^4$ is cyclopentoxycarbonyl.

* * * * *